(12) United States Patent
Suzuki et al.

(10) Patent No.: US 8,043,276 B2
(45) Date of Patent: Oct. 25, 2011

(54) ABSORBENT ARTICLE

(75) Inventors: Migaku Suzuki, Kanagawa (JP); Reiko Moriya, Kanagawa (JP)

(73) Assignee: Japan Absorbent Technology Institute, Tokyo (JP)

( * ) Notice: Subject to any disclaimer, the term of this patent is extended or adjusted under 35 U.S.C. 154(b) by 797 days.

(21) Appl. No.: 11/988,051

(22) PCT Filed: Jun. 30, 2006

(86) PCT No.: PCT/JP2006/313096
§ 371 (c)(1),
(2), (4) Date: Apr. 28, 2008

(87) PCT Pub. No.: WO2007/004561
PCT Pub. Date: Jan. 11, 2007

(65) Prior Publication Data
US 2009/0036852 A1    Feb. 5, 2009

(30) Foreign Application Priority Data
Jul. 1, 2005 (JP) ................................. 2005-193567

(51) Int. Cl.
*A61F 13/15* (2006.01)
(52) U.S. Cl. ......... 604/392; 604/353; 604/397; 604/402
(58) Field of Classification Search .......... 604/347–348, 604/353, 392–402
See application file for complete search history.

(56) References Cited

U.S. PATENT DOCUMENTS

| | | | | |
|---|---|---|---|---|
| 1,609,769 A * | 12/1926 | Perlzweig | ..................... | 604/401 |
| 1,661,936 A * | 3/1928 | Ferstl | ............................ | 604/401 |
| 3,441,024 A * | 4/1969 | Ralph | ............................ | 604/398 |
| 3,452,753 A * | 7/1969 | Sanford | ........................ | 604/401 |
| 5,607,416 A | 3/1997 | Yamamoto et al. | | |
| 5,700,256 A | 12/1997 | Yamamoto et al. | | |
| 6,231,557 B1 | 5/2001 | Krautkramer et al. | | |
| 7,137,972 B1 * | 11/2006 | Holberg | ........................ | 604/392 |
| 2002/0143313 A1 | 10/2002 | Tsuji et al. | | |
| 2007/0287983 A1 * | 12/2007 | Lodge et al. | .................. | 604/402 |

FOREIGN PATENT DOCUMENTS

| | | |
|---|---|---|
| JP | A 6-65409 | 9/1994 |
| JP | A 6-66653 | 9/1994 |
| JP | A 7-96004 | 4/1995 |
| JP | A 7-108047 | 4/1995 |
| JP | A 7-112003 | 5/1995 |
| JP | A 8-56985 | 3/1996 |
| JP | A 8-56986 | 3/1996 |
| JP | A 2002-530152 | 9/2002 |
| JP | A 2002-291800 | 10/2002 |
| JP | A 2002-345871 | 12/2002 |

* cited by examiner

*Primary Examiner* — Lynne Anderson
(74) *Attorney, Agent, or Firm* — Oliff & Berridge, PLC

(57) ABSTRACT

An absorbent article, including: a leak preventer in sheet form having a bottom surface part and a pair of side parts raised upward from both the right and left sides of the bottom surface part and forming an internal space by the bottom surface part and the pair of side parts; an absorber arranged in the internal space at least in one layer, containing a super absorbent polymer, and capable of absorbing body fluids; a pair of side edge stretchable bands provided to extend along edge parts of the pair of side parts; a waist band joined to a rear end of the leak preventer and extending in a lateral direction; and a pair of hip wrapping stretchable bands connected to the pair of side parts of the leak preventer and/or the pair of side edge stretchable bands and to the waist band.

25 Claims, 18 Drawing Sheets (A)

(B)

(C)

(A)

(B)

(A)

(B)

(C)

(A)

(B)

(C)

(A)

(B)

(A)

(B)

(C)

(A)

(B)

(A)

(B)

(C)

(A)

(B)

(C)

ABSORBENT ARTICLE

TECHNICAL FIELD

The present invention relates to a novel absorbent article.

BACKGROUND ART

An absorbent article such as a disposable diaper (for both children and adults), a sanitary napkin, an incontinence product, or training pants is an article for absorbing a body fluid such as urine excreted from a wearer into an absorber employing a super absorbent polymer (hereinafter, may also be referred to as "SAP").

Conventionally, in order to prevent an absorbent article from getting loose to be detached or slipping off from the body of the wearer, various structures have been considered. This problem, however, occurs frequently. Such loosening or slipping off constitutes one of the main causes of leakage at an early stage of wearing. Further, it also leads to the problem of wearing comfort and outward appearance during use being impaired.

Such loosening or slipping off is caused, for example, by a change in the positional relationship between the body of the wearer and the absorbent article due to the breathing of the wearer, a change in his/her position, movement, etc., or deformation of the absorbent article; or a downward force due to a weight load generated when the absorbent article receives human wastes (urine, feces, etc.)

Conventionally, as a means for preventing such loosening and slipping off, in order to hold the absorbent article in intimate contact with the body of the wearer, there has been adopted a method in which an elastic member called waist gather or leg gather (e.g., gusset gather, inner gather, or outer gather) is provided at an edge of the waist part or the crotch part of the absorbent article.

However, it has been impossible to prevent loosening or slipping off to a sufficient degree by such the method.

In view of this, various methods have been proposed.

For example, Patent Documents 1 and 2, proposed by the inventors of the present invention, describe a method according to which the front body part and the rear body part of a tapeless type (shorts type) absorbent article are connected by an elastic member in the vicinity of the waist part or the leg holes.

Further, Patent Documents 3 through 5, proposed by the inventors of the present invention, describe a method according to which an elastic member functioning as a leg gather is provided on the inner side of the leg hole portions of the absorbent article.

Patent Document 1: JP 6-66653 U
Patent Document 2: JP 6-65409 U
Patent Document 3: JP 7-96004 A
Patent Document 4: JP 8-56985 A
Patent Document 5: JP 8-56986 A

DISCLOSURE OF THE INVENTION

Problem to be Solved by the Invention

Though held in highly intimate contact with the thighs, the above-mentioned absorbent articles are not yet to be regarded as satisfactory in terms of the effect of preventing loosening and slipping off.

It is accordingly an object of the present invention to provide an absorbent article capable of preventing loosening and slipping off.

Means for Solving the Problem

After careful study conducted with a view toward achieving the above-mentioned object, the inventors of the present invention have completed an absorbent article of a novel structure.

According to the present invention, there are provided the following absorbent articles according to Items (1) to (25).

(1) An absorbent article, including:

a leak preventer in sheet form having a bottom surface part and a pair of side parts raised upward from both the right and left sides of the bottom surface part and forming an internal space by the bottom surface part and the pair of side parts;

an absorber arranged in the internal space at least in one layer, containing a super absorbent polymer, and capable of absorbing body fluid;

a pair of side edge stretchable bands provided to extend along edge parts of the pair of side parts;

a waist band joined to a rear end of the leak preventer and extending in a lateral direction; and a pair of hip wrapping stretchable bands connected to the pair of side parts of the leak preventer and/or the pair of side edge stretchable bands and to the waist band, in which:

connection parts of the pair of hip wrapping stretchable bands to the pair of side parts of the leak preventer and/or the pair of side edge stretchable bands are positioned at a rear beyond a crotch part; and an interval between the pair of hip wrapping stretchable bands where they are connected to the waist band is larger than an interval between the pair of hip wrapping stretchable bands where they are connected to the pair of side parts of the leak preventer and/or the pair of side edge stretchable bands.

(2) The absorbent article according to Item (1), in which the hip wrapping stretchable bands are integral with the side edge stretchable bands.

(3) An absorbent article, including:

a leak preventer in sheet form having a bottom surface part and a pair of side parts raised upward from both right and left sides of the bottom surface part and forming an internal space by the bottom surface part and the pair of side parts;

an absorber arranged in the internal space at least in one layer, containing a super absorbent polymer, and capable of absorbing body fluid;

a pair of inner walls provided on inner sides of the pair of side parts;

a pair of side edge stretchable bands provided to extend along edge parts of the pair of inner walls;

a waist band joined to a rear end of the leak preventer and extending in a lateral direction; and a pair of hip wrapping stretchable bands provided to extend along edge parts of the pair of side parts and connected to the waist band, in which an interval between the pair of hip wrapping stretchable bands where they are connected to the waist band is larger than an interval between the pair of hip wrapping stretchable bands at a crotch part.

(4) The absorbent article according to any one of Items (1) to (3), in which the side edge stretchable bands are connected to the waist band.

(5) The absorbent article according to any one of Items (1) to (4), in which the side edge stretchable bands include composite bodies formed by covering, with a nonwoven fabric, one or both sides of a plurality of thread-like elastic members arranged in parallel.

(6) The absorbent article according to any one of Items (1) to (5), in which:
the waist band has a width of 30 to 200 mm;
the side edge stretchable bands have a width of 10 to 100 mm; and
the hip wrapping stretchable bands have a width of 5 to 50 mm.

(7) The absorbent article according to any one of Items (1) to (6), in which at least apart of the waist band is a stretchable member.

(8) The absorbent article according to Item (7), in which the waist band has a region of small tensile stress and a region of large tensile stress in that order from a side nearer to the leak preventer to a side farther therefrom.

(9) The absorbent article according to Item (7), in which the waist band has a region of small tensile stress, a region of medium tensile stress, and a region of large tensile stress in that order from a side nearer to the leak preventer to a side farther therefrom.

(10) The absorbent article according to Item (7), in which the waist band has a region of small tensile stress, a region of large tensile stress, and a region of medium tensile stress in that order from a side nearer to the leak preventer to a side farther therefrom.

(11) The absorbent article according to Item (7), in which the waist band has a non-stretchable member at a center in a lateral direction and stretchable members on left and right sides of the non-stretchable member, with the non-stretchable member being connected to the leak preventer.

(12) The absorbent article according to Item (7), in which the waist band is connected to the leak preventer in a lateral direction by a plurality of connection parts.

(13) The absorbent article according to Item (12), in which a length of the leak preventer is larger than a length of the waist band between each of the plurality of connection parts.

(14) The absorbent article according to anyone of Items (1) to (13), further including:
a front waistband connected to a front end of the leak preventer and extending in a lateral direction; and
a pair of front stretchable bands connected to the pair of side parts of the leak preventer and/or the pair of side edge stretchable bands and to the front waist band,
in which an interval between the pair of front stretchable bands where they are connected to the front waist band is larger than an interval between the pair of front stretchable bands where they are connected to the pair of side parts of the leak preventer and/or the pair of side edge stretchable bands thereof.

(15) The absorbent article according to any one of Items (1) to (13), in which the waist band is annular, and is connected to a rear end and a front end of the leak preventer.

(16) The absorbent article according to Item (15), further including a pair of front stretchable bands connected to the pair of side parts of the leak preventer and/or the pair of side edge stretchable bands and to a front end side of the leak preventer of the waist band,
in which an interval between the pair of front stretchable bands where they are connected to the waist band is larger than an interval between the pair of front stretchable bands where they are connected to the pair of side parts of the leak preventer and/or the pair of side edge stretchable bands thereof.

(17) The absorbent article according to Item (14) or (16), in which the front waist band has a width of 5 to 50 mm.

(18) The absorbent article according to any one of Items (1) to (17), further including a bridge member provided to extend between portions corresponding to the crotch parts of the pair of side edge stretchable bands.

(19) An absorbent article according to Item (18), in which the bridge member is in contact with upper surfaces of the side edge stretchable bands.

(20) The absorbent article according to Item (18) or (19), in which the bridge member is in contact with lower surfaces of the side edge stretchable bands.

(21) The absorbent article according to any one of Items (18) to (20), further including a separator connected to a lower side of the bridge member, in which:
the internal space is divided by the separator into a urine absorbing space on a front side and a feces receiving space on a rear side; and
the absorber is arranged in the urine absorbing space.

(22) The absorbent article according to Item (21), in which:
a water-resistant sheet is provided in the feces receiving space; and
a front end portion of the water-resistant sheet is connected to the bridge member to thereby form the separator.

(23) The absorbent article according to Item (22), in which, in the feces receiving space, the absorber is arranged between the leak preventer and the water-resistant sheet.

(24) The absorbent article according to Item (21), in which:
a second absorber is provided in the feces receiving space;
a urine guide member is provided in a vicinity of a front end portion of the second absorber; and
the urine guide member is connected to the bridge member to thereby form the separator.

(25) The absorbent article according to Item (21), in which the separator is a water-resistant sheet connected to the bottom surface part of the leak preventer.

EFFECTS OF THE INVENTION

In the absorbent article of the present invention, loosening and slipping off do not easily occur.

Figure 1:
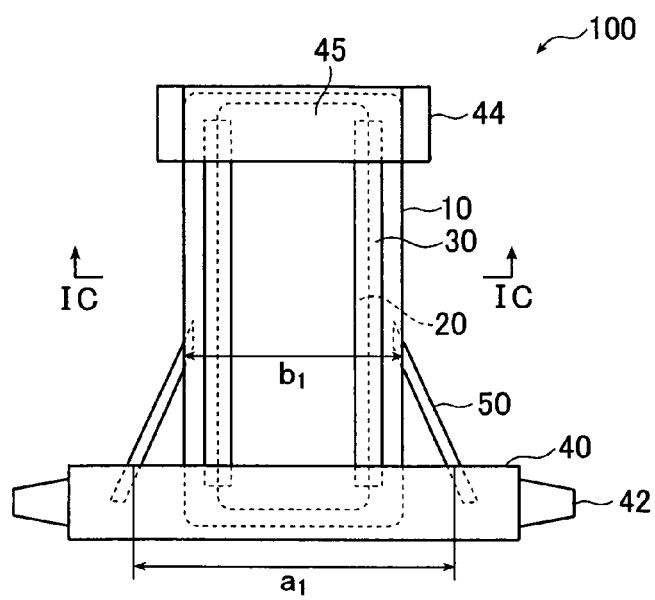
[FIG. 1] Schematic views each showing an example of an absorbent article according to a first aspect of the present invention.
Figure 1:
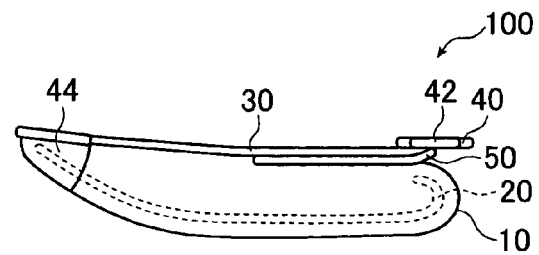
Figure 1:
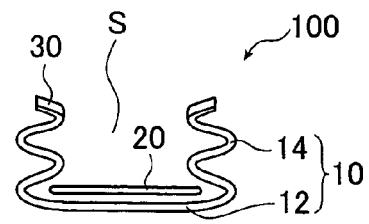

DESCRIPTION OF REFERENCE NUMERALS 10, 10a, 10b, 10c, 10d, 10e, 10f, 10g, 10h, 10i, 10j, 11 leak preventer
12 bottom surface part
14 side part
20, 20a, 20b, 20c absorbent
22, 22a second absorbent
30, 32, 90, 94, 96, 98 side edge stretchable band
40, 400, 402, 404, 406, 408, 410, 412, 414, 416 waist band
42, 42a, 44, 43, 47 attachable/detachable member
45 front leakage prevention portion
46 front waist band
48 annular waist band
50, 80, 90a, 94a, 98a hip wrapping stretchable band
60, 81, 90c, 90d front stretchable band
70 inner wall
90b, 94b, 98b side edge stretchable band extension
96a, 98c, 400b, 408c, 410c, 412d nonwoven fabric
96b stretchable member
100, 110, 200, 300, 310, 320, 350, 360, 370, 380, 390 absorbent article
120, 121, 122 bridge member
125 connection member
130, 132 water-resistant sheet
140 urine guide member
400a polyurethane filament
402a non-stretchable member
402b stretchable member
408a, 410a, 412a member of large tensile stress
408b, 410b, 412c member of small tensile stress
412b member of medium tensile stress
M wearer
S internal space
S1 urine absorbing space
S2 feces receiving space

DETAILED DESCRIPTION OF THE INVENTION

Hereinafter, an absorbent article of the present invention will be described in more detail based on preferable embodiment modes shown in attached drawings. In the specification of the present invention, when the absorbent article is practically worn, a side close to a skin of a wearer is referred to as "upper" side and a side far therefrom is referred to as "lower" side. In addition, when the absorbent article is practically worn, a side corresponding to a front side of a body of a wearer is referred to as "front" and a side corresponding to a rear side thereof is referred to as "rear". In the drawings, members which are practically in contact with each other may be shown to be separately positioned for easy understanding.

FIG. 1 are schematic views each showing an example of an absorbent article according to a first aspect of the present invention. FIG. 1(A) is a plan view. FIG. 1(B) is a left side view, and FIG. 1(C) is a lateral end view taken along the line IC-IC of FIG. 1(A).

Note that, in each plan view of the attached drawings, a front side of an absorbent article or the like is shown on an upper side of the view.

An absorbent article 100 according to the first aspect of the present invention is basically equipped with: a leak preventer 10 in sheet form having a bottom surface part 12 and a pair of side parts 14 raised upwards from both the right and left sides of the bottom surface part 12, the bottom surface part 12 and the pair of side parts 14 forming an internal space S; an absorber 20 arranged in the internal space S at least in one layer, containing super absorbent polymer, and capable of absorbing body fluid; a pair of side edge stretchable bands 30 provided to extend along the edge parts of the pair of side parts 14; a waist band 40 connected to the rear end of the leak preventer 10 and extending in the lateral direction; and a pair of hip wrapping stretchable bands 50 connected to the pair of side parts 14 of the leak preventer 10 and to the waist band 40.

Materials generally used for a back sheet may be used as materials for the leak preventer 10. Specific examples of the materials that can be used include: a resin film of PE, PP, PET, EVA, or the like; and a body fluid impermeable sheet such as a foamed resin sheet made of the resin. Further, a sheet having air permeability such as an air permeable film is preferably used as the body fluid impermeable sheet.

The resin film may be used as a multilayer sheet of the film and a nonwoven fabric for the better touch or appearance. In this case, a spunbond (SB) nonwoven fabric, an SMS nonwoven fabric, a thermal bond nonwoven fabric, or the like having a relatively light weight is preferably used as the nonwoven fabric.

Further, a multilayer sheet of the resin film and an absorber in sheet form described below may be used.

Further, a highly water-resistant nonwoven fabric may be used. In this case, the highly water-resistant nonwoven fabric may be used alone, or used as a multilayer sheet of a film and the highly water-resistant nonwoven fabric.

The leak preventer 10 may be formed of a plurality of members.

As described above, the leak preventer 10 has the bottom surface part 12 and the pair of side parts 14. While in FIG. 1 the pair of side parts 14 are folded starting from the bottom surface part 12, there are no particular limitations in this regard as long as they are raised upwards from both the right and left sides of the bottom surface part 12.

The internal space S is formed by the bottom surface part 12 and the pair of side parts 14. The absorber 20 is arranged in the internal space S.

There are no particular limitations regarding the absorber used in the present invention as long as it contains super absorbent polymer and is capable of absorbing body fluid. For example, it is possible to use an absorber in powder form such as powdery wood pulp and unprocessed SAP; however, taking into consideration stability in form, risk of falling off, etc., an absorber in sheet form is preferable. Above all, it is desirable to adopt an absorber in sheet form formed by coating nonwoven fabric with the super absorbent polymer.

The kind of absorber can be selected as appropriate according to the use. For example, when the absorbent article of the present invention is used as a diaper for children, an absorber containing a large amount of wood pulp is preferable for newborn babies and a few month old babies (small-size), and an absorber containing large amount of SAP is preferable for several month old babies (medium-size or large-size).

In a preferred mode, the absorber in sheet form is a super absorbent sheet containing 50 wt % or more SAP, preferably 60 to 95 wt % SAP.

The super absorbent sheet is an ultrathin absorber in sheet form containing SAP as a main component. The super absorbent sheet has a very high SAP content, and thus is very thin. The super absorbent sheet has a thickness of preferably 1.5 mm or less, more preferably 1 mm or less.

A structure or a production process for the super absorbent sheet is not particularly limited as long as the super absorbent sheet is an ultrathin absorber in sheet form containing SAP as a main component.

An example of the super absorbent sheet includes a super absorbent sheet obtained by an Air Laid process. The Air Laid process involves mixing pulverized wood pulp and SAP, adding a binder, and forming the mixture into a sheet, to thereby obtain a super absorbent sheet. Examples of the super absorbent sheet obtained by this process include: NOVATHIN (US registered trademark) manufactured by Rayonier Inc.; and B-SAP manufactured by Oji Kinocloth Co., Ltd.

Another example of the super absorbent sheet includes a super absorbent sheet obtained by a process involving coating SAP-dispersed slurry on a body fluid permeable sheet such as a nonwoven fabric. The SAP-dispersed slurry is preferably prepared by dispersing SAP and microfibrillated cellulose (MFC) in a mixed solvent of water and ethanol. An example of the super absorbent sheet obtained by this process includes MegaThin (Japanese registered trademark) manufactured by Japan Absorbent Technology Institute.

Other examples of the super absorbent sheet include: a super absorbent sheet obtained by a process involving carrying a large amount of SAP on a raised nonwoven fabric and fixing the SAP with a hot melt binder, an emulsion binder, an aqueous fiber, or the like; a super absorbent sheet obtained through a process involving mixing fibrous SAP with a polyethylene terephthalate (PET) fiber and forming the mixture into a web; and an SAP sheet obtained by providing tissues above and below an SAP layer.

The absorber is provided in at least one layer. That is, the absorber may be provided as one layer, or as two or more layers (multilayer).

Further, the absorber may be provided while being folded.

The pair of side edge stretchable bands 30 are provided at the respective edge portions of the pair of side parts 14 so as to extend along the edge portions. While in FIG. 1 the side edge stretchable bands 30 are provided to extend over the entire length of the edge portions, the present invention is not restricted to this construction. It is also possible to provide no side edge stretchable bands near the end portions on the front and rear sides of the end portions.

When, as shown in FIG. 1, the side edge stretchable bands 30 are connected to the waist band 40, wearing the absorbent article 100 of the present invention results in the side edge stretchable bands 30 being pulled in the longitudinal direction thereof by the waist band 40, so the side edge stretchable bands 30 are brought into intimate contact with the body of the wearer. Further, the side edge stretchable bands 30 follow any movement of the wearer, and is not easily detached from the body of the wearer, so it is possible to prevent leakage of urine and feces more effectively.

Regarding the side edge stretchable bands 30 as long as they are stretchable members; it is desirable for the upper surfaces thereof to be substantially flat so that they may be held in intimate contact with the hips of the wearer to suppress discomfort.

In a preferable mode, for example, they include composite members formed by covering one or both sides of a plurality of thread-like elastic members arranged in parallel with nonwoven fabric.

Further, it is possible to adopt the same construction as that in the case described below in which the waist band is stretchable.

While there are no particular limitations regarding the width of the side edge stretchable bands, it preferably ranges from 10 to 100 mm.

The waist band 40 is connected to the rear end of the leak preventer 10 and extends in the lateral direction. The waist band serves to fix the absorbent article of the present invention in position while keeping it in intimate contact with the body of the wearer.

While there are no particular limitations regarding the material of the waist band 40, it is desirable for at least a part thereof to include a stretchable member. Its material, structure, etc. will be described below.

While there are no particular limitations regarding the width of the waist band, it preferably ranges from 30 to 200 mm.

In the absorbent article 100, attachable/detachable members 42 are provided at both the right and left ends of the waist band 40. The attachable/detachable members 42 as well as an attachable/detachable member 44 provided at the forward end of the waist band 40 are attachable and detachable to each other. For example, they may be formed by various types of surface fastener.

When the user wears the absorbent article 100, the attachable/detachable members 42 and the attachable/detachable member 44 are connected together, whereby a waist hole is formed by the waist band 40 and the front end portion of the leak preventer 10.

In the absorbent article 100, a front leak preventer portion 45 is provided at the front end of the leak preventer 10.

The front leak preventer portion 45 is connected to the bottom surface part 12 of the leak preventer 10 and the side edge stretchable bands 30 to form a bag part, whereby leakage of urine and feces from the front side is prevented more effectively.

The pair of hip wrapping stretchable bands 50 are connected to the pair of side parts 14 of the leak preventer 10 and the waist band 40. The connection parts of the pair of hip wrapping stretchable bands 50 to the pair of side parts 14 are at the rear beyond the crotch part. Further, the interval between the pair of hip wrapping stretchable bands 50 where they are connected to the waist band 40 (indicated by reference symbol $a_1$ of FIG. 1) is larger than the interval between the pair of hip wrapping stretchable bands 50 where they are connected to the pair of side parts 14 of the leak preventer 10 (indicated by reference symbol $b_1$ of FIG. 1).

While in the absorbent article 100 the hip wrapping stretchable bands 50 are connected to the pair of side parts 14 of the leak preventer 10, they may also be connected to the pair of side edge stretchable bands 30 or to both of the pairs.

The hip wrapping stretchable bands 50 are stretchable members. Its material, structure, etc. may be the same as those in the case described below in which the waist band is a stretchable member.

While there are no particular limitations regarding the width of the hip wrapping stretchable bands, the width preferably ranges from 5 to 50 mm.

Figure 2:
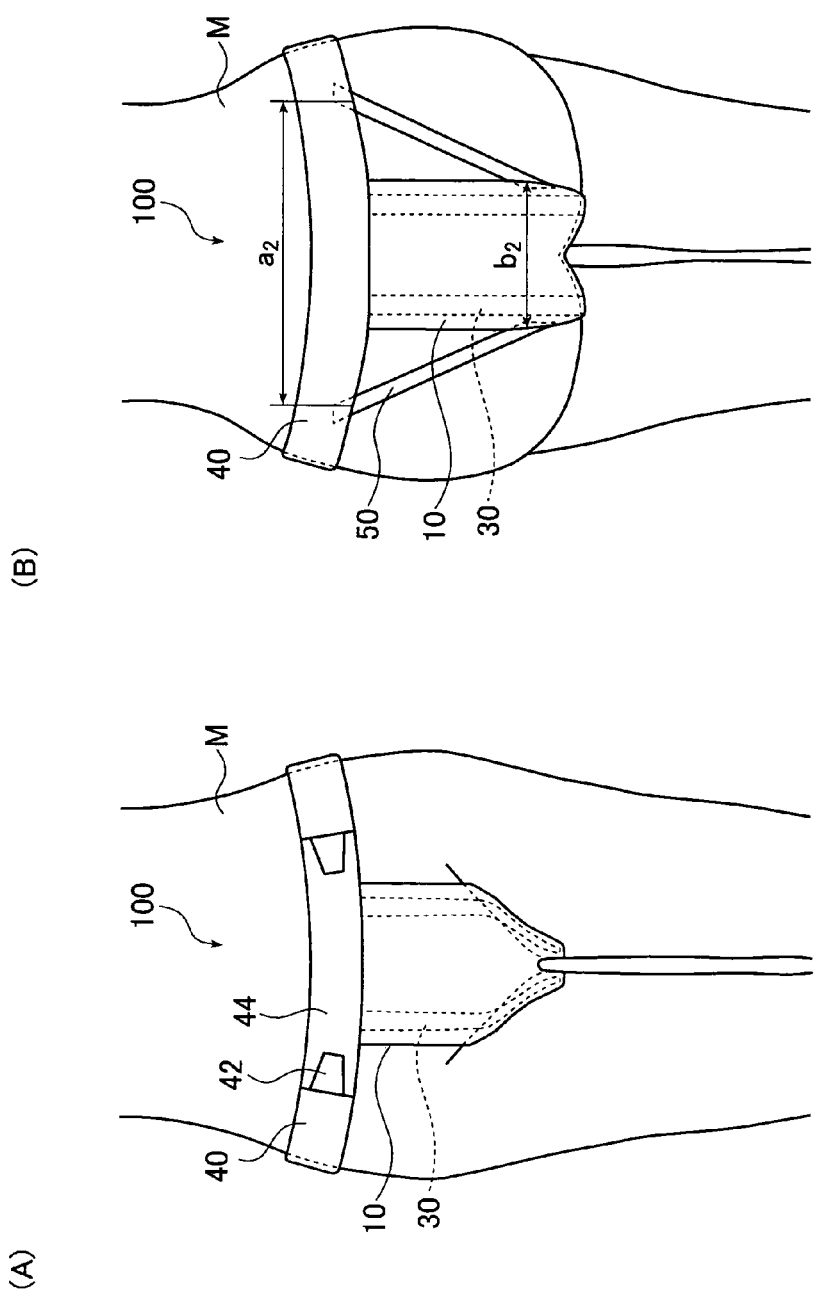
[FIG. 2] Schematic views each showing how an absorbent article according to the first aspect of the present invention is worn by a person.

FIG. 2 are schematic views as seen from the front side and the rear side of the wearer when the absorbent article 100 of the first aspect of the present invention is worn by the wearer. FIG. 2(A) is a schematic view as seen from the front side of the wearer, and FIG. 2(B) is a schematic view as seen from the rear side of the wearer.

As shown in FIG. 2, since the side edge stretchable bands 30 are stretchable members, they are held in intimate contact with the body of the wearer M when the absorbent article 100 of the present invention is worn. Thus, not loosening or slipping off occurs.

Further, in the absorbent article 100 of the present invention, on the rear side of the wearer, the pair of side edge stretchable bands 30 provided to extend along the edge portions of the pair of side parts 14 of the leak preventer 10 are positioned to extend substantially in parallel along the curves of the hips of the wearer M. On the front side of the wearer while positioned substantially in parallel in the upper portion, the pair of side edge stretchable bands 30 are reduced in the interval therebetween at the crotch part of the wearer M. This is due to the narrowing of the crotch part of the wearer. Thus, also on the rear side, the portions of the pair of side edge stretchable bands 30 near the crotch part are pulled inwardly.

The curves of the hips of the wearer form a depression toward the center of the wearer, so if there are no hip wrapping stretchable bands 50, the pair of side edge stretchable bands 30 are likely to drop in the inner side of the hips. When one or both of the side edge stretchable bands drop in the inner side of the hips, there will be an increased risk of leakage of urine and feces.

On the rear side of the absorbent article 100, the hip wrapping stretchable bands 50 are provided between the side edge stretchable bands 30 and the waist band 40, and the interval between them gradually increases as they extend upwards (e.g., $a_2 > b_2$ in FIG. 2). Since the hip wrapping stretchable bands 50 are stretchable members, they serve to pull the side edge stretchable bands 30 upwards and outwards on the rear side of the absorbent article 100, whereby it is possible to effectively prevent loosening and slipping off of the side edge stretchable bands 30. Further, an appropriate distance is maintained between the pair of side edge stretchable bands 30 to prevent them from dropping in, smoothening the absorption or reception of urine and feces by the absorber 20.

Further, while the absorbent article 100 of the present invention is worn, the hip wrapping stretchable bands 50 are positioned along the curves of the hips of the wearer M, thus softly wrapping the hips. Thus, unlike the leg gathers of a conventional absorbent article, they do not tighten the groin to hinder the blood flow.

An absorbent article according to a preferred aspect of the present invention further includes a front waistband connected to the front end of the leak preventer and extending in the lateral direction, and a pair of front stretchable bands connected to the pair of side parts of the leak preventer and/or the pair of side edge stretchable bands and to the front waist band, with the interval between the pair of front stretchable bands where they are connected to the front waist band being larger than the interval between the pair of front stretchable bands where they are connected to the pair of side parts of the leak preventer and/or the pair of side edge stretchable bands.

Figure 3:
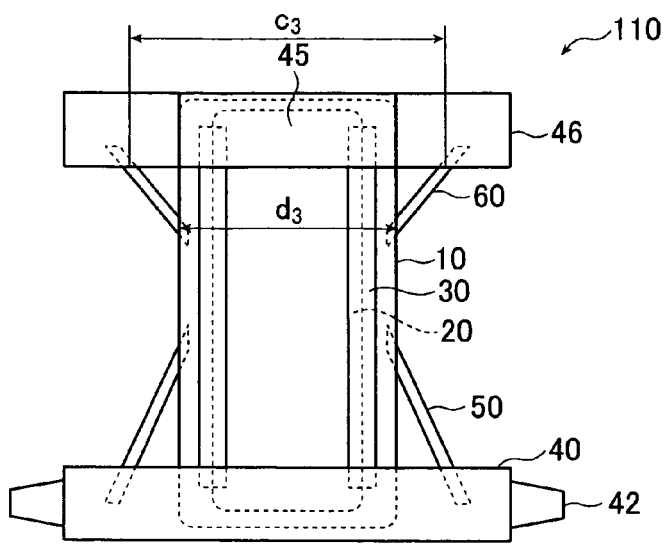
[FIG. 3] Schematic views each showing another example of an absorbent article according to the first aspect of the present invention.
Figure 3:
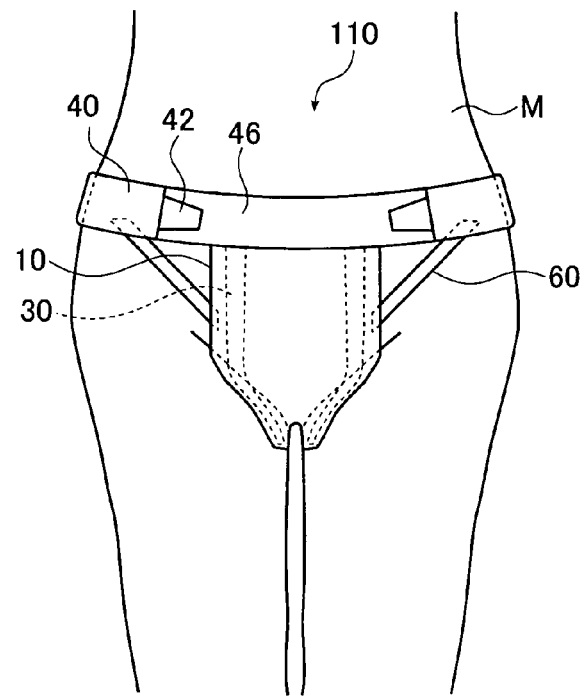

FIG. 3 are schematic views each showing an absorbent article according to the first aspect of the present invention. FIG. 3(A) is a plan view, and FIG. 3(B) is a front view as seen from the front side of the wearer when the absorbent article is worn by the user.

While it is basically the same as the absorbent article 100, an absorbent article 110 shown in FIG. 3(A) is equipped with a front waist band 46 connected to the front end of the leak preventer 10 and extending in the lateral direction, and a pair of front stretchable bands 60 connected to the pair of side parts 14 of the leak preventer 10 and the front waist band 46. In the absorbent article 110, the interval between the pair of front stretchable bands 60 where they are connected to the front waist band 46 (indicated by reference symbol $c_3$ of FIG. 3) is larger than the interval between the pair of front stretchable bands 60 where they are connected to the pair of side parts 14 of the leak preventer 10 (indicated by reference symbol $d_3$ of FIG. 3).

The front stretchable bands 60 are stretchable members, so, as shown in FIG. 3(B), when in use, they serve to pull the side edge stretchable bands 30 upwards and outwards on the front side of the absorbent article 110, whereby it is possible to still more effectively prevent loosening or slipping off of the side edge stretchable bands 30. Further, an appropriate interval is maintained between the pair of side edge stretchable bands 30, whereby the absorption or reception of urine and feces by the absorbent 20 is smoothened.

Further, as shown in FIG. 3(B), in the absorbent article 110 of the present invention, it is desirable for the front stretchable bands 60 to be positioned above the groin of the wearer M when in use. In this case, unlike the leg gathers of a conventional absorbent article, they do not tighten the groin to hinder the blood flow.

The front stretchable bands 60 are stretchable members. Their material, structure, etc. may be the same as those of the hip wrapping stretchable bands 50. The preferable width of the front stretchable bands ranges, for example, from 5 to 50 mm.

Figure 4:
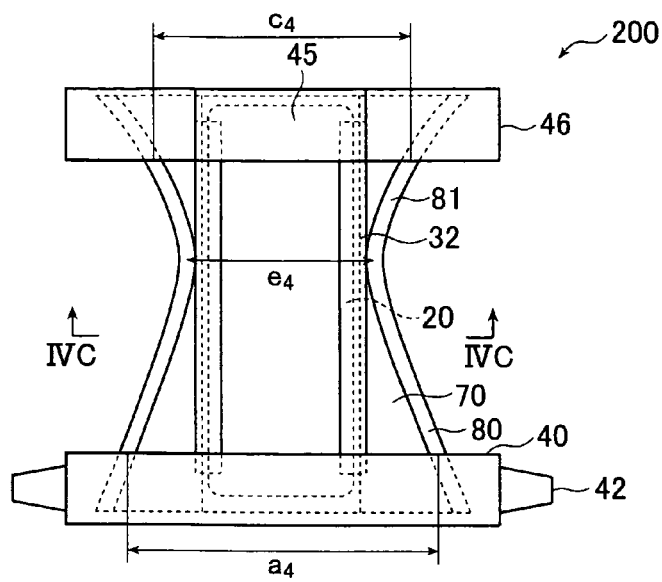
[FIG. 4] Schematic views each showing an example of an absorbent article according to a second aspect of the present invention.
Figure 4:
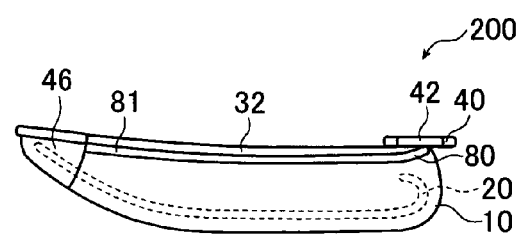
Figure 4:
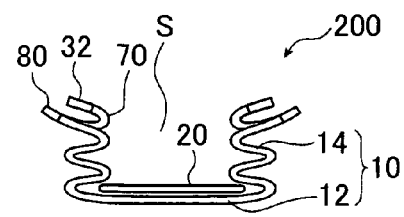

FIG. 4 are schematic views each showing an example of an absorbent article according to a second aspect of the present invention. FIG. 4(A) is a plan view. FIG. 4(B) is a left side view, and FIG. 4(C) is a lateral end view taken along the line IVC-IVC of FIG. 4(A).

As shown in FIG. 4, an absorbent article 200 according to the second aspect of the present invention is basically equipped with: a leak preventer 10 in sheet form having a bottom surface part 12 and a pair of side parts 14 raised upwards from both the right and left sides of the bottom surface part 12, the bottom surface part 12 and the pair of side parts 14 forming the internal space S; an absorber 20 arranged in the internal space S at least in one layer, containing super absorbent polymer, and capable of absorbing body fluid; a pair of inner walls 70 provided on the inner sides of the pair of side parts 14; a pair of side edge stretchable bands 32 provided to extend along the edge portions of the pair of inner walls 70; a waist band 40 connected to the rear end of the leak preventer 10 and extending in the lateral direction; and a pair of hip wrapping stretchable bands 80 provided to extend along the edge portions of the pair of side parts 14 and connected to the waist band 40; along with a pair of front stretchable bands 81.

The leak preventer 10, the absorber 20, and the waist band 40 are the same as those of the absorbent article 100 of the first aspect of the present invention.

That is, while it is basically the same as the absorbent article 100, the absorbent article 200 differs therefrom in that it is equipped with the pair of inner walls 70 provided on the inner sides of the pair of side parts 14, the pair of side edge stretchable bands 32 being provided to extend along the edge portions of the pair of inner walls 70, the pair of hip wrapping stretchable bands 80 being connected to the pair of side parts 14 and the waist band 40, the pair of front stretchable bands 81 being connected to the pair of side parts 14 and the front waist band 46, the hip wrapping stretchable bands 80 and the front stretchable bands 81 being integrated.

There are no particular limitations regarding the material of the inner walls 70. Both a liquid permeable material and a liquid impermeable material can be adopted.

The side edge stretchable bands 32 may be the same as the side edge stretchable bands 30.

As shown in FIG. 4, in the absorbent article 200, the interval between the pair of hip wrapping stretchable bands 80 where they are connected to the waist band 40 (indicated by reference symbol $a_4$ of FIG. 4) is larger than the interval between the hip wrapping stretchable bands 80 at the crotch part (indicated by reference symbol $e_4$ of FIG. 4).

Figure 5:
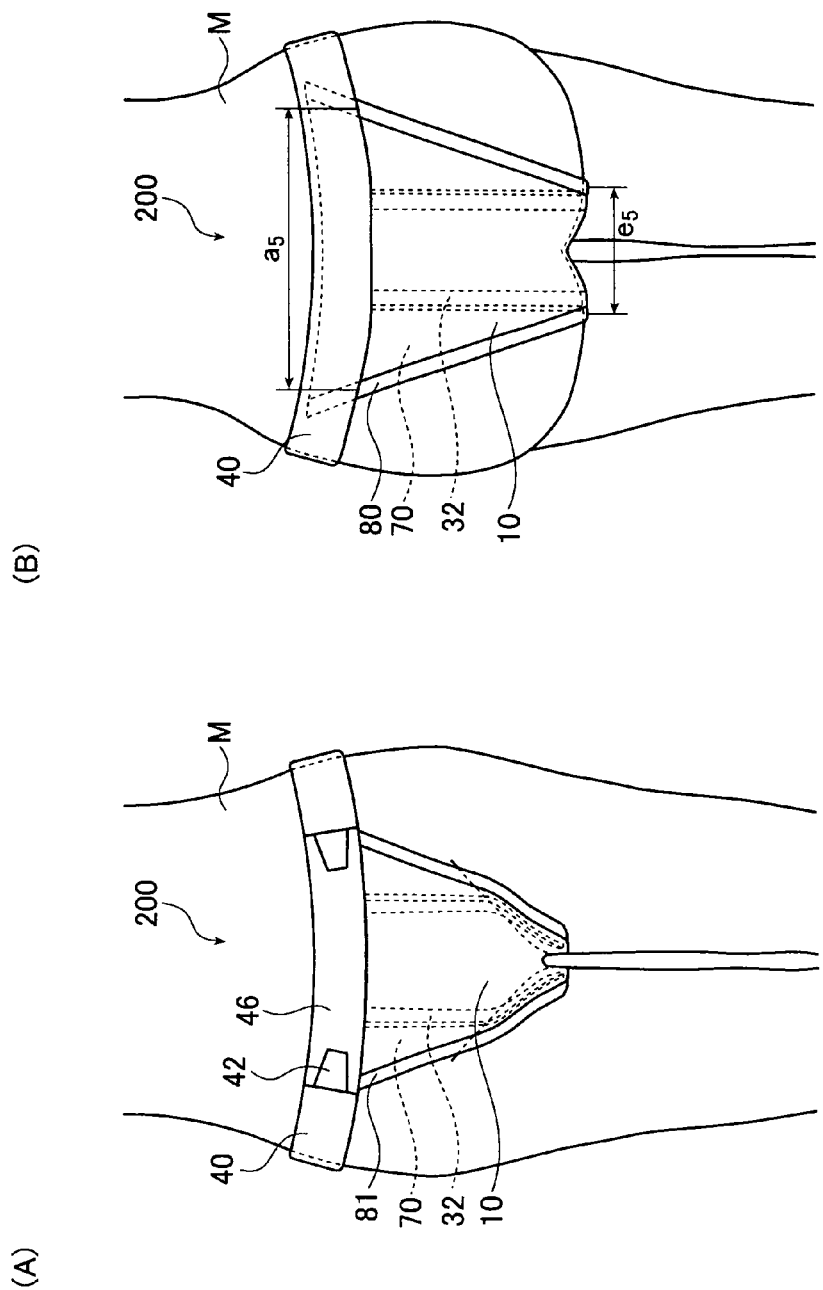
[FIG. 5] Schematic views each showing how an absorbent article according to the second aspect of the present invention is worn by a person.

FIG. 5 are schematic views as seen from the front side and the rear side of the wearer when the absorbent article 200 of the second aspect of the present invention is worn by the wearer. FIG. 5(A) is a schematic view as seen from the front side of the wearer, and FIG. 5(B) is a schematic view as seen from the rear side of the wearer.

As shown in FIG. 5, since the side edge stretchable bands 32 are stretchable members, they are held in intimate contact with the body of the wearer M when the absorbent article 200 of the present invention is worn. Thus, not loosening or slipping off occurs.

Further, in the absorbent article 200, on the rear side of the wearer, the pair of side edge stretchable bands 32 provided to extend along the edge portions of the pair of side parts 14 of the leak preventer 10 are positioned to extend substantially in parallel along the curves of the hips of the wearer M. On the front side of the wearer while positioned substantially in parallel in the upper portion, the pair of side edge stretchable bands 32 are reduced in the interval therebetween at the crotch part of the wearer M. This is due to the narrowing of the crotch part of the wearer. Thus, also on the rear side, the portions of the pair of side edge stretchable bands 32 near the crotch part are pulled inwardly.

The curves of the hips of the wearer form a depression toward the center of the wearer, so if there are no hip wrapping stretchable bands 80, the pair of side edge stretchable bands 32 are likely to drop in the inner side of the hips. When one or both of the side edge stretchable bands drop in on the inner side of the hips, there will be an increased risk of leakage of urine and feces and the side edge stretchable bands 32 will come into direct contact with the urethral meatus and the anus of the wearer to cause discomfort.

In the absorbent article 200, the pair of inner walls 70 are provided on the respective inner sides of the pair of side parts 14, the pair of side edge stretchable bands 32 are provided to extend along the respective edge portions of the pair of inner walls 70, and the pair of hip wrapping stretchable bands 80 are connected to the pair of side parts 14 and the waist band 40. Further, the interval between the pair of hip wrapping stretchable bands 80 where they are connected to the waist band 40 (indicated by reference symbol $a_5$ of FIG. 5) is larger than the interval between the pair of hip wrapping stretchable bands 80 at the crotch part (indicated by reference symbol $e_5$ of FIG. 5).

The hip wrapping stretchable bands 80 are stretchable members, so, on the rear side of the absorbent article 200, they serve to pull the side stretchable bands 32 upwards and outwards via the side parts 14 and the inner walls 70, whereby loosening and slipping off of the side edge stretchable bands 32 are prevented more effectively. Further, an appropriate interval is maintained between the pair of side edge stretchable bands 32 through the side parts 14 and the inner walls 70 to prevent them from dropping in the inner side, thereby smoothening the absorption or reception of urine and feces by the absorbent 20.

Further, in the absorbent article 200, the hip wrapping stretchable bands 80 are positioned to extend along the curves of the hips of the wearer M during use, thus softly wrapping the hips. Thus, unlike the leg gathers of a conventional absorbent article, they do not tighten the groin to hinder the blood flow.

It is desirable for the tensile stress in the longitudinal direction of the hip wrapping stretchable bands 80 to be smaller than the tensile stress in the longitudinal direction of the side edge stretchable bands 32. In this case, there is no risk of the tensile stress of the hip wrapping stretchable bands 80 being too strong to exert an unnecessarily large force on the side edge stretchable bands 32 to thereby cause deviation.

Further, as shown in FIG. 4, in the absorbent article 200, not only do the hip wrapping stretchable bands 80 exist beyond the crotch part, but the front stretchable bands 81, integrated with the hip wrapping stretchable bands 80, exist to extend forward from the crotch part. Further, the interval between the pair of front stretchable bands 81 where they are connected to the front waist band 46 (indicated by reference symbol $c_4$ of FIG. 4) is larger than the interval between the pair of front stretchable bands 81 at the crotch part (indicated by reference symbol $e_4$ of FIG. 4).

As stated above, the front stretchable bands 81 are stretchable members, so, as shown in FIG. 5(A), on the front side of the absorbent article 200, they serve to pull the side edge stretchable bands 32 upwardly and outwardly via the side parts 14 and the inner walls 70 during use, whereby loosening and slipping off of the side stretchable bands 32 are prevented still more effectively. Further, an appropriate interval is maintained between the pair of side edge stretchable bands 32 through the side parts 14 and the inner walls 70, thereby smoothening the absorption or reception of urine and feces by the absorber 20.

While, in the absorbent article of the second aspect of the present invention, the hip wrapping stretchable bands may just exist on the rear side beyond the crotch part, it is also possible, as in the case of the absorbent article 200, for the front stretchable bands, integrally with the hip wrapping stretchable bands, to exist so as to extend forward from the crotch part.

Next, various modes of the hip wrapping stretchable bands will be described.

Figure 6:
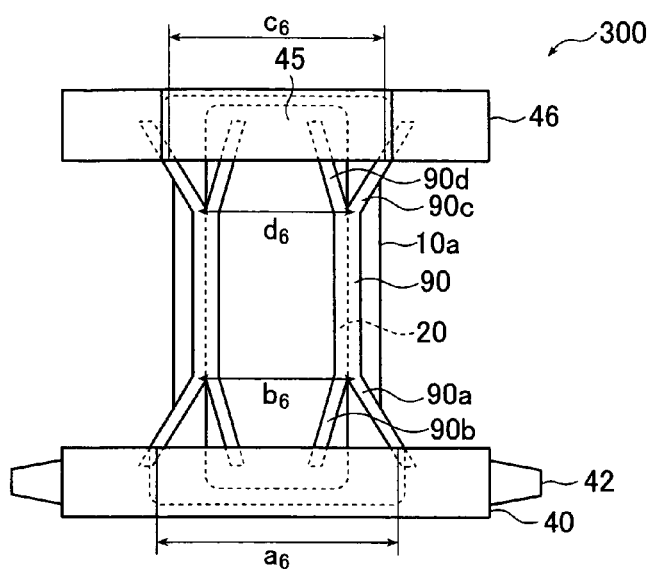
[FIG. 6] A schematic plan view of another example of an absorbent article according to the first aspect of the present invention.

FIG. 6 is a schematic plan view of another example of the absorbent article of the first aspect of the present invention.

In an absorbent article 300 shown in FIG. 6, which is basically the same as the absorbent article 110, the edge portions of the pair of side parts of a leak preventer 10a are widened in the lateral direction on the front and rear sides from the central portion. Further, the rear end portions of a pair of side edge stretchable bands 90 branch off into two portions at the rear beyond the crotch part to form hip wrapping stretchable bands 90$a$ and side edge stretchable band extensions 90$b$. Further, the hip wrapping stretchable bands 90$a$ are provided along the edge portions of the pair of side parts of the leak preventer 10$a$, and the side edge stretchable band extensions 90$b$ are separated from the leak preventer 10$a$ to be connected to the central portion of the waist band 40.

In the absorbent article 300, the interval between the hip wrapping stretchable bands 90$a$ where they are connected to the waist band 40 (indicated by reference symbol $a_6$ of FIG. 6) is larger than the interval between the hip wrapping stretchable bands 90$a$ where they are connected to the pair of side edge stretchable bands 90 (branching part) (indicated by reference symbol $b_6$ of FIG. 6), whereby the same effect as that of the absorbent article 110 described above can be attained.

As shown in the drawing, the hip wrapping stretchable bands 90$a$ and the side edge stretchable band extensions 90$b$ may be substantially of the same width or of different widths.

Figure 9:
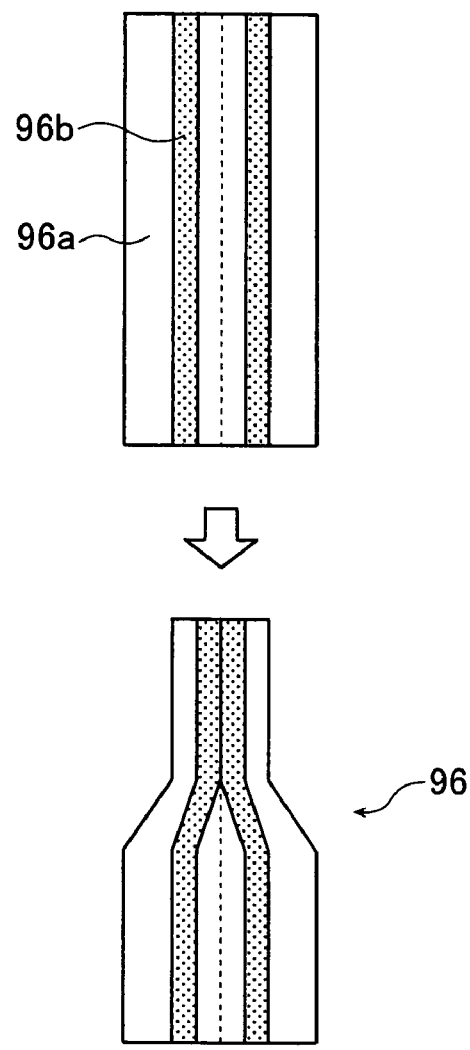
[FIG. 9] A schematic explanatory view illustrating a method of manufacturing a side edge stretchable band according to another mode.
Figure 10:
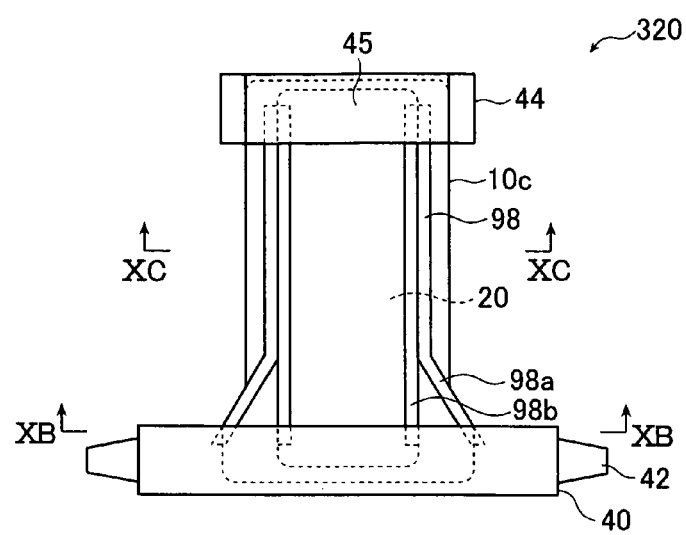
[FIG. 10] Schematic views each showing another example of an absorbent article according to the first aspect of the present invention in which side edge stretchable bands and the hip wrapping stretchable bands are integrated with each other.
Figure 10:
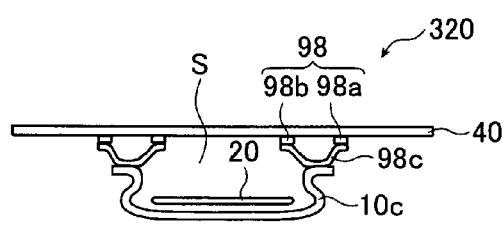
Figure 10:
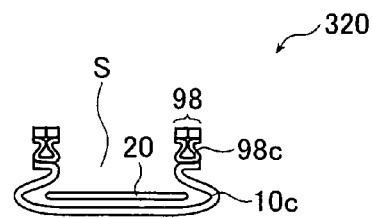

As in the case of side edge stretchable bands 96 shown in FIG. 9 and side edge stretchable bands 98 shown in FIG. 10, nonwoven fabric may be arranged between the hip wrapping stretchable bands 90$a$ and the side edge stretchable band extensions 90$b$.

When, as in the case of the absorbent article 300, the hip wrapping stretchable bands are formed such that each of the waist band side end portions of the side edge stretchable bands branches off into two or more portions, the three-dimensional hips of the wearer are supported at a plurality of different angles by the hip wrapping stretchable bands and the side edge stretchable bands. As a result, the side edge stretchable bands are less subject to deviation from the body of the wearer, so an appropriate interval between the side edge stretchable bands is easily maintained, the absorption or reception of urine and feces by the absorbent is further smoothened, and the area of the hips of the wearer stained with urine and feces is reduced.

Further, the branching can be effected solely by providing cuts at an end of each hip wrapping stretchable band, so its manufacture is facilitated.

Further, in the absorbent article 300, each of the front end portions of the pair of side edge stretchable bands 90 branches off into two portions in front of the crotch part to form front stretchable bands 90$c$ and 90$d$. Further, the outer front stretchable bands 90$c$ are provided to extend along the edge portions of the pair of side parts of leak preventer 10$a$, and the inner front stretchable bands 90$d$ are separated from the leak preventer 10$a$ to be connected to the central portion of the front waist band 46.

In the absorbent article 300, the interval between the outer front stretchable bands 90$c$ where they are connected to the front waist band 46 (indicated by reference symbol $c_6$ of FIG. 6) is larger than the interval between the outer front stretchable bands 90$c$ where they are connected to the pair of side edge stretchable parts 90 (branching parts) (indicated by reference symbol $d_6$ of FIG. 6), whereby the same effect as that of the absorbent article 110 described above can be obtained.

As shown in the drawing, the outer front stretchable bands 90$c$ and the inner front stretchable bands 90$d$ may be substantially of the same width or of different widths.

Nonwoven fabric may be arranged between the outer front stretchable bands 90$c$ and the inner front stretchable bands 90$d$.

There are no particular limitations regarding the branching angles on the front and rear sides of the side edge stretchable bands 90; they may be the same or different.

As described above, in the absorbent article 300, the side edge stretchable bands 90 branch off on both the front and rear sides; however, a mode in which branching off is effected only on the rear side is also suitably applicable.

Figure 7:
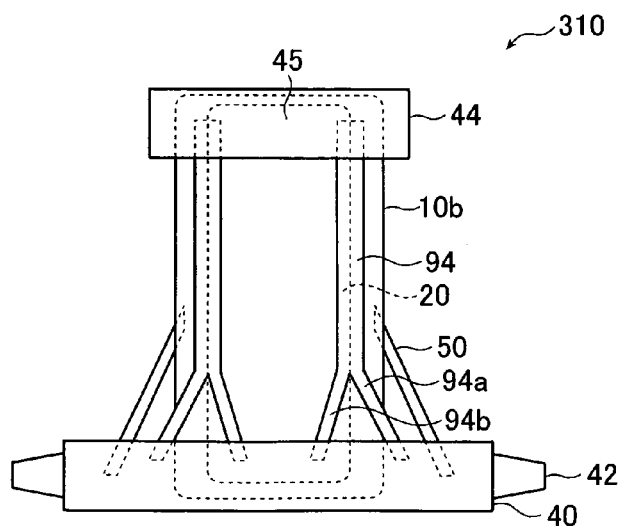
[FIG. 7] A schematic plan view of another example of an absorbent article according to the first aspect of the present invention.

FIG. 7 is a schematic plan view of another example of the absorbent article of the first aspect of the present invention.

In an absorbent article 310 shown in FIG. 7, which is basically the same as the absorbent article 100, the rear end portions of a pair of side edge stretchable bands 94 branch off into two portions at the rear beyond the crotch part to form hip wrapping stretchable bands 94$a$ and side edge stretchable band extensions 94$b$. Further, the hip wrapping stretchable bands 94$a$ are provided along the edge portions of the pair of side parts of the leak preventer 10$b$, and the side edge stretchable band extensions 94$b$ are separated from the leak preventer 10$b$ to be connected to the central portion of the waist band 40.

Further, like the absorbent article 100, the absorbent article 310 has the hip wrapping stretchable bands 50.

In the present invention, when a plurality of hip wrapping stretchable bands are provided (for example, when there are provided both hip wrapping stretchable bands connected to the side edge stretchable bands and hip wrapping stretchable bands connected to the side parts of the leak preventer), it is only necessary for the outermost hip wrapping stretchable bands to satisfy the following condition: the interval between the pair of hip wrapping stretchable bands where they are connected to the waist band is larger than the interval between the hip wrapping stretchable bands where they are connected to the pair of side parts of the leak preventer and/or the pair of side edge stretchable bands.

As in the absorbent article 310, when there are provided both hip wrapping stretchable bands connected to the side edge stretchable bands and hip wrapping stretchable bands connected to the side parts of the leak preventer, it is possible to effectively prevent the absorbent article from being downwardly detached from the body of the wearer as a result of its becoming heavier due to discharge of urine and feces.

It is also possible for the side edge stretchable band extensions 94$b$ to be connected to the rear end portion of the leak preventer 10$b$ but not connected to the waist band 40. In this case, a part or all of the side edge stretchable band extensions 94$b$ may not be stretchable.

A preferred method of manufacturing side edge stretchable bands for a case in which the side edge stretchable bands and the hip wrapping stretchable bands are integrated will be described.

Figure 8:
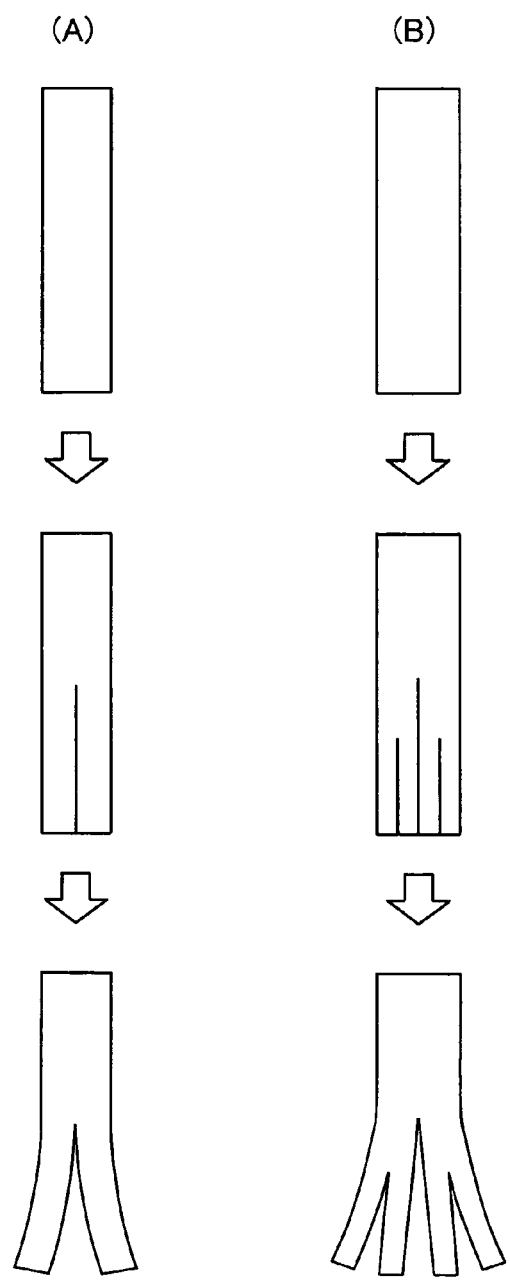
[FIG. 8] Schematic explanatory views each illustrating a method of manufacturing a side edge stretchable band whose one end portion branches off into two or more portions.

FIG. 8 are schematic explanatory views each illustrating a method of manufacturing a side edge stretchable band whose one end portion branches off into two or more portions. FIG. 8(A) illustrates a method of manufacturing a side edge stretchable band whose one end portion branches off into two portions, and FIG. 8(B) illustrates a method of manufacturing a side edge stretchable band whose one end portion branches off into four portions.

By the method shown in FIG. 8(A), an end portion of a band-like member shown in the top diagram is provided a cut in the longitudinal direction as shown in the middle diagram. As shown in the bottom diagram, the two portions obtained by branching off are connected to a waist band or the like.

By the method shown in FIG. 8(B), which is similar to the one shown in FIG. 8(A), a band-like member branches off into four portions by cuts.

FIG. 9 is a schematic explanatory view illustrating a method of manufacturing a side edge stretchable band according to another mode.

A side edge stretchable member 96 manufactured by the method shown in FIG. 9 is formed by using a member in which two stretchable members 96b are bonded to nonwoven fabric 96a so as to extend parallel to the longitudinal direction. As shown in the bottom diagram, the end portions of this member are folded such that the two stretchable members 96b are brought into contact with each other on the dotted line in the drawing, and glued together in this state by an adhesive prepared beforehand for integration. The nonwoven fabric 96a is a highly water-resistant nonwoven fabric.

Unlike the case in which a single stretchable member is divided, in the side edge stretchable band 96 constructed as described above, there exits nonwoven fabric between the portion functioning as the side edge stretchable band and the portion functioning as the hip wrapping stretchable band, so in case urine and feces are allowed to get out of the side edge stretchable band, they are trapped between the side edge stretchable band and the hip wrapping stretchable band, and do not leak to the outside.

FIG. 10 are schematic views each showing an example of an absorbent article according to the first aspect of the present invention in which the side edge stretchable bands and the hip wrapping stretchable bands are integrated. FIG. 10(A) is a plan view, FIG. 10(B) is a cross-sectional view taken along the line XB-XB of FIG. 10(A), and FIG. 10(C) is a cross-sectional view taken along the line XC-XC of FIG. 10(A).

Each of side edge stretchable bands 98 used in an absorbent article 320 shown in FIG. 10 is obtained by bonding two stretchable members to a nonwoven fabric 98c so as to extend in parallel in the longitudinal direction, folding the end portions so as to bring the two stretchable members into contact with each other, and bonding them together in this state by an adhesive applied beforehand to integrate them. The integrated portion constitutes the side edge stretchable band 98; the portion where the two stretchable members are separated from each other serve as a hip wrapping stretchable band 98a and a side edge stretchable band 98b. The nonwoven fabric 98c is a highly water-resistant nonwoven fabric.

Basically, the absorbent article 320 is equipped with a leak preventer 10c in sheet form having a bottom surface part and a pair of side parts raised upwards from both the right and left sides of the bottom surface part, the bottom surface part and the pair of side parts forming an internal space S, an absorber 20 arranged in the internal space S at least in one layer, containing a super absorbent polymer, and capable of absorbing body fluid, a pair of side edge stretchable bands 98 provided to extend along the respective edge portions of the pair of side parts, the waist band 40 connected to the rear end of the leak preventer 10c and extending in the lateral direction, the pair of side edge stretchable bands 98, and the hip wrapping stretchable bands 98a and the side edge stretchable band extensions 98b connected to the waist band 40.

As is apparent from FIGS. 10(B) and 10(C), in the absorbent article 320, the pair of side parts of the leak preventer 10c is formed by the right and left edge portions of the leak preventer and the nonwoven fabrics 98c.

In this construction, the thin nonwoven fabrics 98c connect the side edge stretchable bands 98 and the leak preventer, so the movement of the side edge stretchable bands 98 is not hindered by the absorber 20 and the leak preventer 10c, which are of relatively high rigidity, and they can easily follow the movement of the body of the wearer. Further, it is possible to prevent the absorber 20 from being wrinkled by the movement of the side edge stretchable bands 98.

Next, various modes of the waist band will be illustrated.

As stated above, it is desirable for the waist band to be a stretchable member. This helps to further enhance the intimacy with which the body of the wearer and the absorbent article of the present invention are held in contact with each other.

Examples of the stretchable material that can be used include natural rubber, synthetic rubber, polyurethane, polyolefin-based elastomer (e.g., SEBS and SIS), and polyester-based elastomer. Those materials may take, for example, a film-like, filament-like, net-like, or nonwoven-fabric-like form. A composite material including a stretchable material in the above-mentioned form and a nonwoven fabric can also be suitably applied.

Specific examples of the waist band include (i) one in which a plurality of filament-like stretchable members of polyurethane filament (e.g., Lycra manufactured by DuPont), natural rubber filament or the like are arranged in parallel, with both sides being held by nonwoven fabric, (ii) a one-way stretchable elastic composite body in which polyurethane filaments and a stretchable nonwoven fabric are stacked together (e.g., one as described in JP 7-252762 A), (iii) the one obtained by stacking together in a streak-like fashion a net-like structure of SEBS (manufactured, for example, by Conwed Plastics, Inc. of the United States) and a nonwoven fabric (e.g., one described in JP 10-195746 A), and (iv) a spunbond of polyurethane fiber (e.g., Espansione manufactured by Kanebo, Ltd.).

Figure 11:
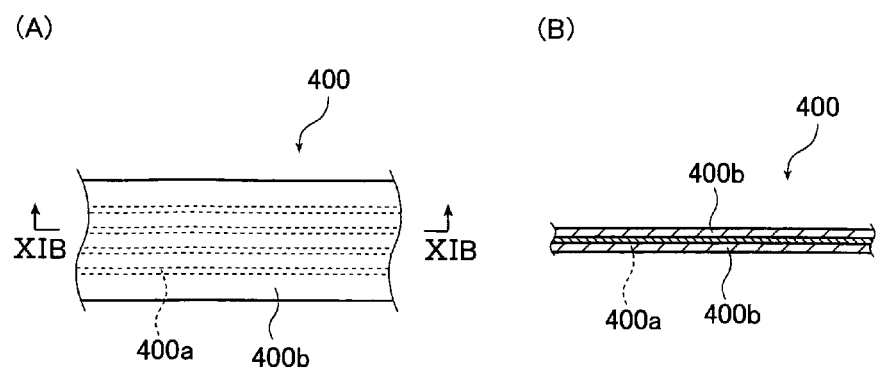
[FIG. 11] Schematic views each showing example of a waist band in which a number of filament-like stretchable members are arranged in parallel and held on both sides by nonwoven fabric.

FIG. 11 are schematic views each showing an example of the waist band in which a plurality of filament-like stretchable members are arranged in parallel with both sides held by nonwoven fabric (the above-mentioned example (i)). FIG. 11(A) is a plan view, and FIG. 11(B) is a cross-sectional view taken along the line XIB-XIB of FIG. 11(A).

In a waist band 400 shown in FIG. 11, a plurality of polyurethane filaments 400a are arranged in parallel, with both sides thereof being held by nonwoven fabrics 400b. Preferred examples of the nonwoven fabrics 400b include SMS nonwoven fabric. The weight of the nonwoven fabric preferably ranges from 10 to 30 g/m².

In the case in which the waist band is a stretchable member, it is desirable for the stress at 50% expansion in the lateral direction to be 10 to 20 g/cm, with the width (length in the front-to-rear direction) being 30 mm or more. With the above-mentioned range, no slipping off occurs if the absorbent article becomes heavy due to urine and feces after long use, nor is there large tightening feel involved.

A preferable range of the stress at 50% expansion in the lateral direction of the waist band is 15 g/cm or less since that will involve less tightening feel.

The width of the waist band is preferably 50 mm or more since that will help to enhance the above-mentioned effect. The width of the waist band is preferably 200 mm or less from the viewpoint of cost.

In the case in which the waist band is a stretchable member, it may be formed by a combination of members differing in stretchability in the width direction (front-to-rear direction) and/or the lateral direction.

Figure 12:
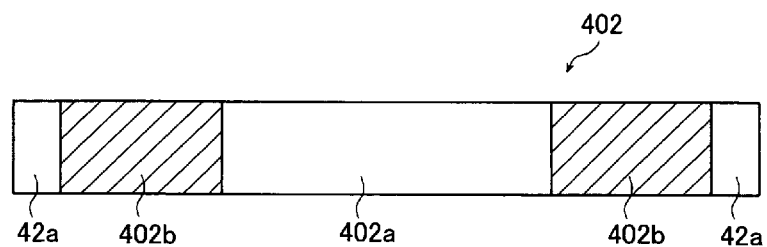
[FIG. 12] A schematic plan view of a waist band formed by a combination of members differing in stretchability in the lateral direction.

FIG. 12 is a schematic plan view of an example of a waist band formed by a combination of members differing in stretchability in the lateral direction.

A waist band 402 shown in FIG. 12 is formed by a non-stretchable member 402a at the center and stretchable members 402b arranged on the right and left sides thereof. Attachable/detachable members 42a are provided at the right and left ends of the waist band 402.

In this mode, it is desirable for the non-stretchable member 402a to be connected to the leak preventer, with the stretchable members 402b being capable of stretching freely.

Figure 13:
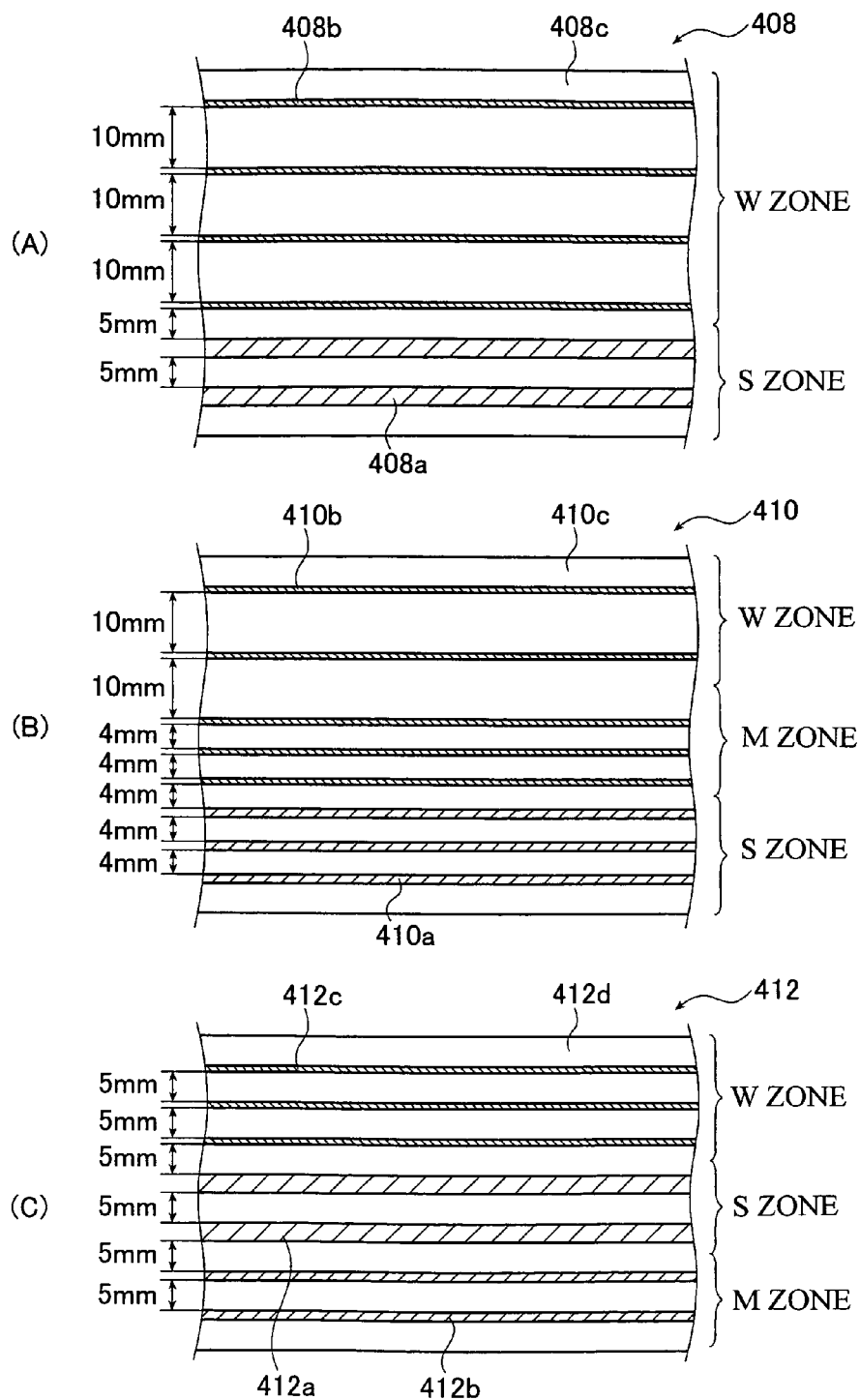
[FIG. 13] Schematic plan views each showing various examples of a waist band formed by a combination of members differing in stretchability in the width direction (front-to-rear direction).

FIG. 13 are schematic plan views each showing various examples of the waist band formed by a combination of members differing in stretchability in the width direction (front-to-rear direction).

In a waist band 408 shown in FIG. 13(A), two members 408a of large tensile stress are arranged in parallel on the rear side at intervals of 5 mm, and four members 408b of small tensile stress are arranged in parallel on the front side at intervals of 10 mm, with the upper and lower sides of the band being held by nonwoven fabrics 408c (the upper nonwoven fabric is not shown).

The two members 408a of large tensile stress form a region of large tensile stress (S-zone), and the four members 408b of small tensile stress form a region of small tensile strength (W-zone).

As the members 408a of large tensile stress, it is possible to use, for example, rubber bands having a width of 3 mm and a thickness of 200 μm. As the members 408b of small tensile stress, it is possible to use, for example, polyurethane yarns of 800 dtex.

When the waist band thus has a region of small tensile stress and a region of large tensile stress in that order from the side nearer to the leak preventer to the side farther therefrom, both regions can be brought into intimate contact with portions of different peripheral lengths such as the curved abdominal region, the hips, and the depressed waist portion, with appropriate tension.

In a waist band 410 shown in FIG. 13(B), three members 410a of large tensile stress are arranged in parallel on the rear side at intervals of 4 mm, a total of five members 410b of small tensile stress are arranged in parallel in the intermediate portion at intervals of 4 mm and on the front side at intervals of 10 mm, with the upper and lower sides of the band being held between nonwoven fabrics 410c (the upper nonwoven fabric is not shown).

The two members 410a of large tensile stress form a region of large tensile stress (S-zone), and the five members 408b of small tensile stress form a region of medium tensile stress (M-zone) in the intermediate portion, and a region of small tensile stress (W-zone) on the front side.

As the members 410a of large tensile stress, it is possible to use, for example, polyurethane yarns of 1200 dtex. As the members 410b of small tensile stress, it is possible, for example, to use polyurethane yarns of 600 dtex.

When the waist band thus has a region of small tensile stress, a region of medium tensile stress, and a region of large tensile stress in that order from the side nearer to the leak preventer to the side farther therefrom, the regions can be brought into intimate contact with the body of the wearer successively differing in peripheral lengths from the curved abdominal region or the hips to the depressed waist portion, with appropriate tension.

In a waist band 412 shown in FIG. 13(C), two members 412a of large tensile stress are arranged in parallel at the center at intervals of 5 mm, two members 412b of medium tensile stress are arranged in parallel on the rear side at intervals of 5 mm, and three members 412c of small tensile stress are arranged in parallel on the front side at intervals of 5 mm, with the upper and lower sides of the band being held between nonwoven fabrics 412d (the upper nonwoven fabric is not shown).

The two members 412a of large tensile stress form a region of large tensile stress (S-zone), the two members 412b of medium tensile stress form a region of medium tensile stress (M-zone), and the three members 412c of small tensile stress form a region of small tensile stress (W-zone).

As the members 412a of large tensile stress, it is possible to use, for example, rubber bands having a width of 3 mm and a thickness of 200 μm. As the members 412b of medium tensile stress, it is possible to use, for example, polyurethane yarns of 1200 dtex. As the members 412c of small tensile stress, it is possible, for example, to use polyurethane yarns of 600 dtex.

When the waist band thus has a region of small tensile stress, a region of large tensile stress, and a region of medium tensile stress in that order from the side nearer to the leak preventer to the side farther therefrom, the regions can be brought into intimate contact with portions of different peripheral lengths such as the curved abdominal region and hips, the depressed waist portion, and the somewhat swollen upper waist portion (near the navel), with appropriate tension.

As shown in FIGS. 13(A) through 13(C), it is desirable for the W-zone to be on the front side of the waist band. The side edge stretchable bands and an the hip wrapping stretchable bands are connected to the front side of the waist band, and it is desirable to connect them to the W-zone of small tensile stress so that their movement may not be restricted.

A method of varying stretchability in the width direction of the waist band is not restricted to the above-described examples, and various other methods are available.

For example, the following methods (i) through (v) may be suitably adopted, in all of which the width of the waist band is assumed to be approximately 80 mm.

(i) A method in which, when using one type of polyurethane yarns (e.g., 600 dtex), S-zone is formed through arrangement at intervals of 3 mm, M-zone is formed through arrangement at intervals of 6 mm, and W-zone is formed through arrangement at intervals of 10 mm.

(ii) A method in which, when arranging three types of polyurethane yarns at equal intervals (e.g., 5 mm), S-zone is formed with fat polyurethane yarns (e.g., 1200 dtex), M-zone is formed with polyurethane yarns of medium thickness (e.g., 800 dtex), and W-zone is formed with thin polyurethane yarns (e.g., 500 dtex).

(iii) A method in which, when using rubber bands of a fixed thickness (e.g., 150 μm), S-zone is formed with wide rubber bands (having a width of, for example, 5 mm), M-zone is formed with rubber bands of medium width (having a width of, for example, 3 mm), and W-zone is formed with narrow rubber bands (having a width of, for example, 1 mm).

(iv) A method in which, when combining rubber bands (having a thickness of, for example, 150 μm) with polyurethane films (having a thickness of, for example, 100 μm), S-zone is formed with rubber bands (having a width of, for example, 5 mm), M-zone is formed with wide polyurethane films (having a width of, for example, 5 mm), and W-zone is formed with narrow polyurethane films (having a width of, for example, 2 mm).

(v) A method in which, when combining rubber bands (having a thickness of, for example, 150 μm) with polyurethane yarns (e.g., 1200 dtex), S-zone is formed with rubber bands (having a width of, for example, 3 mm), M-zone is formed by arranging polyurethane yarns at intervals of 3 mm, and W-zone is formed by arranging polyurethane yarns at intervals of 10 mm.

While each of those examples includes a waist band having three zones differing in stretchability in the width direction, it is also possible to adopt a waist band having one zone less, i.e., two zones.

Next, various modes of the connection between the stretchable waist band and the leak preventer will be described.

Figure 14:
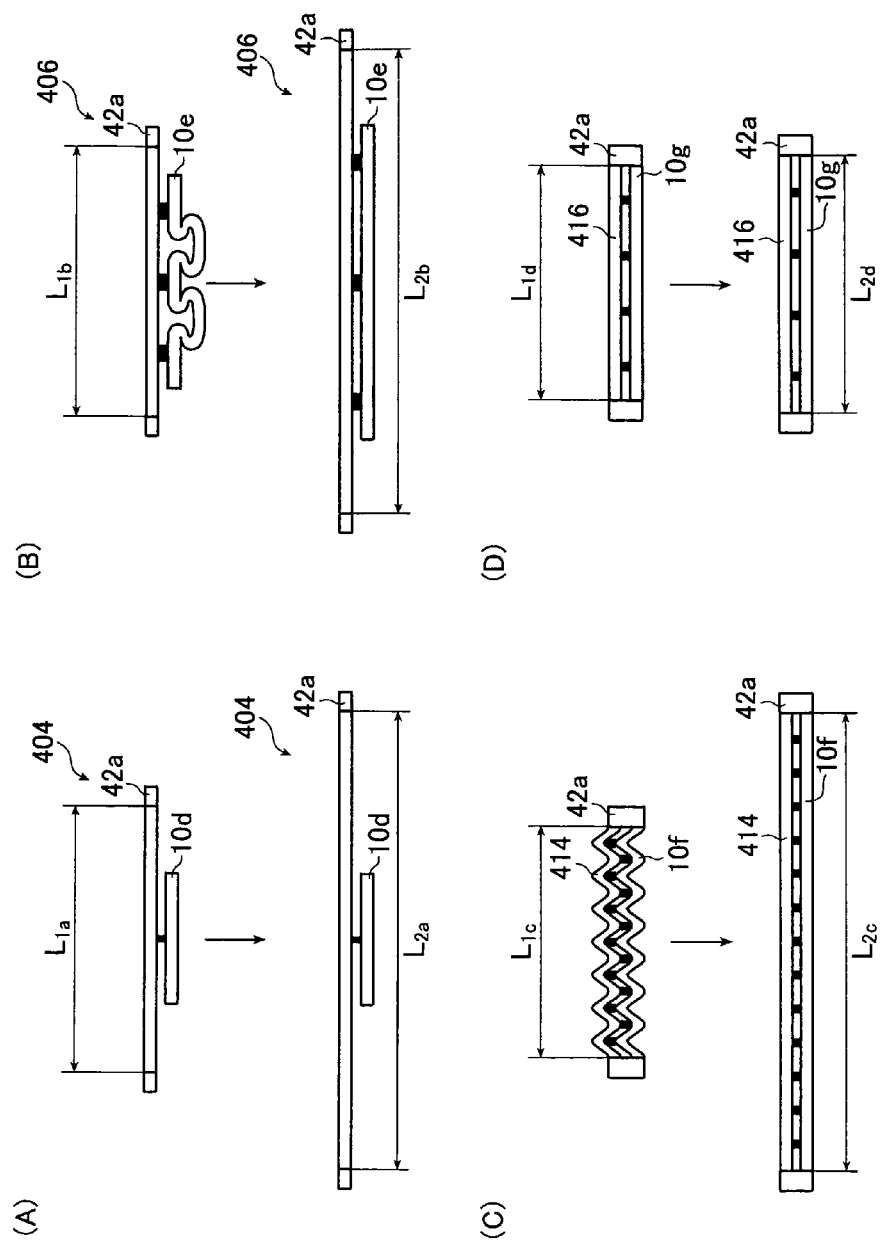
[FIG. 14] Schematic sectional views each showing various examples of a waist band and a leak preventer connected together.

FIG. 14 are schematic sectional views each showing various examples of the waist band and the leak preventer connected to each other. In FIG. 14, the portions filled in with black indicate adhesive. In all of FIGS. 14(A) through 14(D), the upper diagram shows the state before use, and the lower diagram shows the state during use.

FIG. 14(A) shows a waist band 404 including a stretchable member only, and a leak preventer 10d connected thereto. As shown in FIG. 14(A), only the central portion of the waist band 404 is connected to the leak preventer 10d. Prior to wearing, the waist band is in the state as shown in the upper diagram, whereas, during wearing, the waist band 404 expands without being constrained from the outside as shown in the lower diagram. The ratio of the length $L_{2a}$ of the waist band 404 during use to the length $L_{1a}$ of the waist band 404 before use is approximately 2.0 to 3.0 at the maximum (in the case in which it is assumed that the expansion of the stretchable member is 2.0 to 3.0 at the maximum; this applies also to the following cases).

In this way, when the waist band as a whole is a stretchable member and only one portion thereof is connected to the leak preventer, there is no constraint from the leak preventer, which is a non-stretchable member, so it is advantageously possible to increase the expansion of the waist band.

FIG. 14(B) shows a waist band 406 including a stretchable member only, and a leak preventer 10e connected thereto. As shown in FIG. 14(B), the waist band 406 is connected to the leak preventer 10e at three positions. The waist band 406, which is in the state as shown in the upper diagram before use, expands when in use as shown in the lower diagram. The leak preventer 10e, which is folded before use, is unfolded when in use. Thus, the leak preventer 10e does not practically affect the free expansion of the waist band 406.

The ratio of the length $L_{2b}$ of the waist band 406 when in use with respect to the length $L_{1b}$ thereof before use is approximately 1.8 to 2.8 at the maximum.

When the waist band as a whole is thus formed as a stretchable member, it is advantageously possible to expand the waist band to a large degree.

As shown in FIG. 14(B), in those cases, it is desirable for the length of the leak preventer to be larger than the length of the waist band between each of the plurality of connection parts. In this case, there is little constraint from the leak preventer, which is a non-stretchable member, so the expansion of the waist band can be effected more smoothly.

FIG. 14(C) shows a waist band 414 and a leak preventer 10f connected thereto. As shown in FIG. 14(C), the waist band 414 includes a stretchable member only, which is connected to the leak preventer 10f by point bonding over the entire length in the lateral direction. More specifically, the waist band 414 is stretched under stress, and is, in this state, bonded to the leak preventer 10f (it contracts when the stress is removed). The waist band 414, which is in the state as shown in the upper diagram before use, expands during uses as shown in the lower diagram, and the leak preventer 10f is also stretched. However, since the waist band 414 is bonded to the leak preventer 10f at a number of positions, its expansion is substantially restricted.

The ratio of the length $L_{2c}$ of the waist band 404 when in use with respect to the length $L_{1c}$ thereof before use is approximately 1.3 to 1.6 at the maximum.

FIG. 14(D) shows a waist band 416 and a leak preventer 10g connected thereto. As shown in FIG. 14(D), the waist band 416 includes a stretchable member only, and is connected to the leak preventer 10g at three positions by point bonding. Before use, the whole of the waist band is in the state as shown in the upper diagram; during use, the leak preventer 10g, which is non-stretchable, prevents expansion of the waist band 416 as shown in the lower diagram.

The ratio of the length $L_{2d}$ of the waist band 416 when in use with respect to the length $L_{1d}$ thereof before use is approximately 1.1 to 1.2 at the maximum.

When using a stretchable waist band, in order to exert its stretchability to the utmost, it is desirable for the waist band to be connected to the leak preventer in the modes as shown in FIGS. 14(A) and 14(B). In this case, it is possible to utilize the "floating structure" as proposed by the inventors of the present invention in JP 5-228177 A.

Next, various modes of the attachable/detachable members will be described.

There are no particular limitations regarding the material of the attachable/detachable members, and it is possible to adopt a conventionally well-known material. Examples of the material include adhesive tape and surface fastener (e.g., hook/loop type).

There are no particular limitations regarding the structure of the attachable/detachable members, and it is possible to adopt a conventionally well-known structure.

Figure 15:
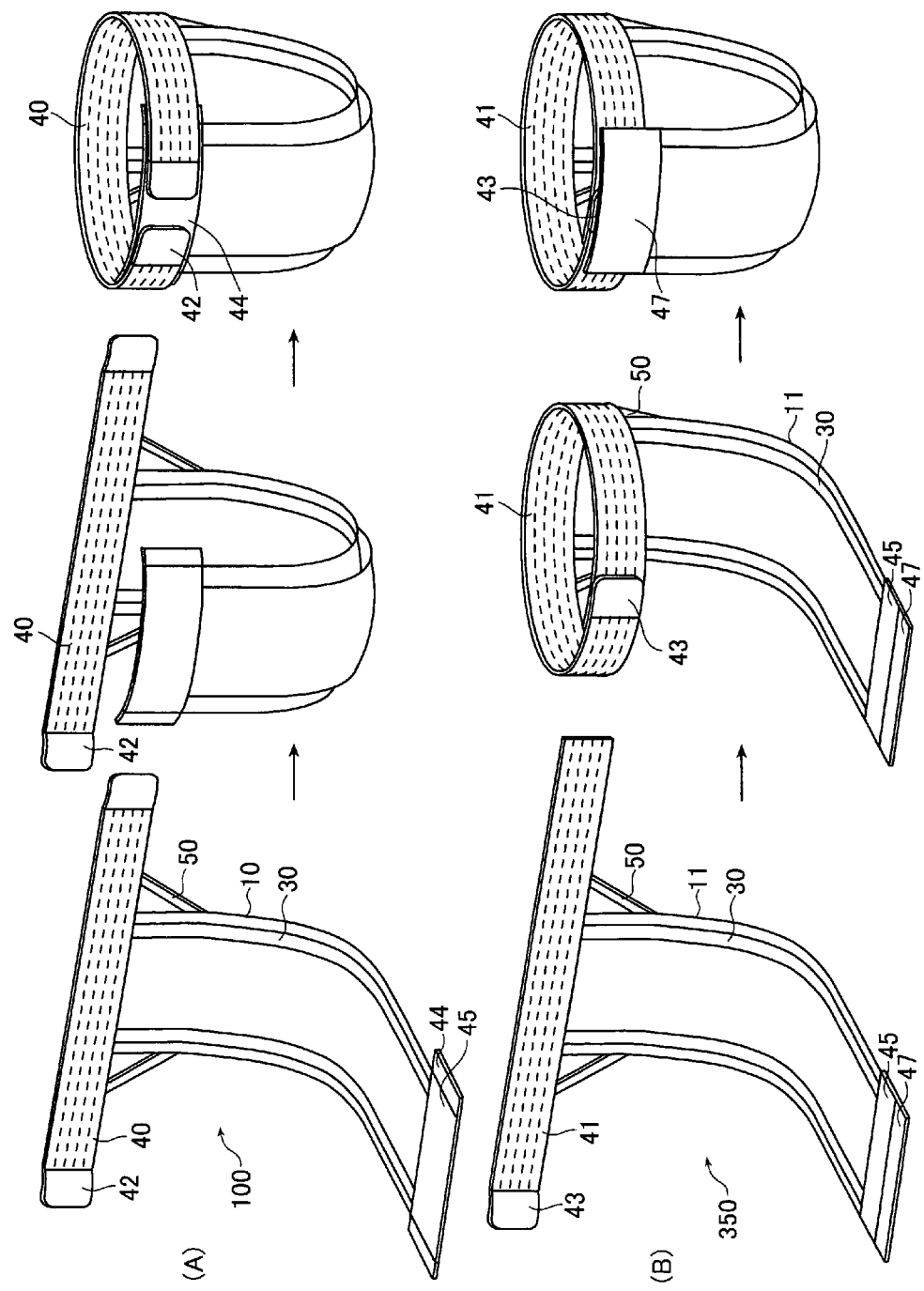
[FIG. 15] Schematic perspective views each showing an example of an absorbent article having various attachable/detachable members.

FIG. 15 are schematic perspective views showing examples of absorbent articles having various attachable/detachable members.

The left-hand diagram of FIG. 15(A) show the absorbent article 100 as shown in FIG. 1. When wearing the absorbent article 100, the absorbent article 100 is first passed between the legs of the wearer to bring it into contact with the body of the wearer (see the middle diagram of FIG. 15(A)). Then, the attachable/detachable members 42 provided at the right and left ends of the waist band 40 are detachably connected to the attachable/detachable members 44 provided at the front end of the leak preventer 10, whereby the wearing is completed (see the right-hand diagram of FIG. 15(A)).

Examples of the materials of the attachable/detachable members include a combination of hooks provided on the inner surfaces (the upper surfaces in FIG. 1) of the attachable/detachable members 42 and loops provided on the outer surface of the attachable/detachable member 44. The combination of the loops and the hooks may be reversed.

The left-hand diagram of FIG. 15(B) show an absorbent article 350, which is basically the same as the absorbent article 100 but which differs therefrom in the attachable/detachable members. More specifically, the outer surface of a waist band 41 and the inner surface of an attachable/detachable member 43 provided at one end of the waist band 41 can be detachably attached to each other. Further, the inner surface of an attachable/detachable member 47 provided at the front end of the leak preventer 11 and the outer surface of the waist band 41 can be detachably attached to each other.

When wearing the absorbent article 350, the absorbent article 350 is first passed between the legs of the wearer, and is brought into contact with the body of the wearer, with the attachable/detachable member 43 being connected to the opposite side of the waist band 41 (see the middle diagram of FIG. 15(B)). Then, the attachable/detachable member 47 is connected to the waist band 41, whereby the wearing is completed (see the right diagram of FIG. 15(B)).

Examples of the materials of the attachable/detachable members include a combination of hooks provided on the inner surface of the attachable/detachable member 43 and on the inner surface of the attachable/detachable member 47 and loops provided on the outer surface of the waist band 41. The combination of the loops and hooks may be reversed.

The waist band may be of an annular configuration and be connected to the rear end and the front end of the leak preventer.

Figure 16:
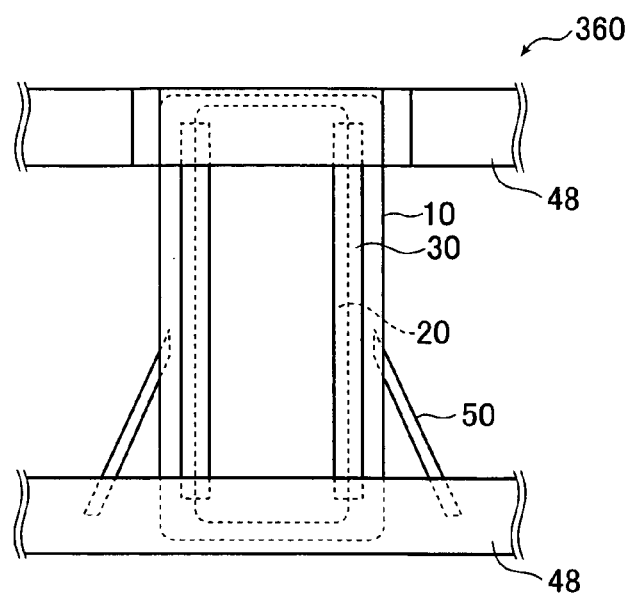
[FIG. 16] Schematic views each showing an example of an absorbent article according to the first aspect of the present invention having an annular waist band.
Figure 16:
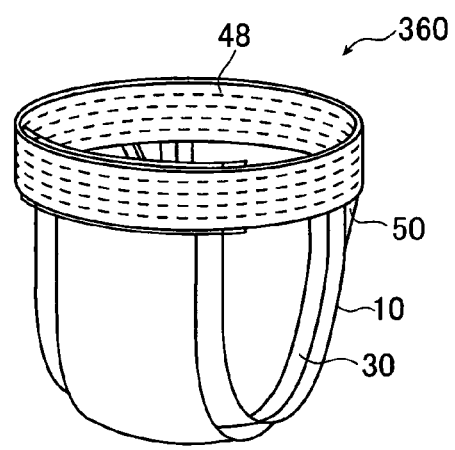

FIG. 16 are schematic views each showing an example of an absorbent article according to the first aspect of the present invention having an annular waist band.

FIG. 16 show an absorbent article 360, which is basically the same as the absorbent article 100 but which differs therefrom in that an annular waist band 48 is connected not only to the rear end but also to the front end of the leak preventer.

FIG. 16(A) is a plan view of the absorbent article 360 whose waist band 48 is shown as cut off, and FIG. 16(B) is a perspective view of the absorbent article 360.

As in the case of the absorbent article 360 shown in FIG. 16, the absorbent article of the first and second modes of the present invention may be formed as an absorbent article having an annular waist band, that is, as a so-called shorts type absorbent article. In this case, it is possible to provide the above-mentioned front stretchable bands, and it is desirable for the interval between the pair of front stretchable bands where they are connected to the waist band to be larger than the interval between the pair of front stretchable bands where they are connected to the pair of side parts of the leak preventer and/or the pair of side edge stretchable bands. It is desirable for the width of the front stretchable bands to range from 5 to 50 mm.

An absorbent article according to a preferred aspect of the present invention is further equipped with a bridge member provided to extend between the portions corresponding to the crotch part of the pair of side edge stretchable bands.

Figure 17:
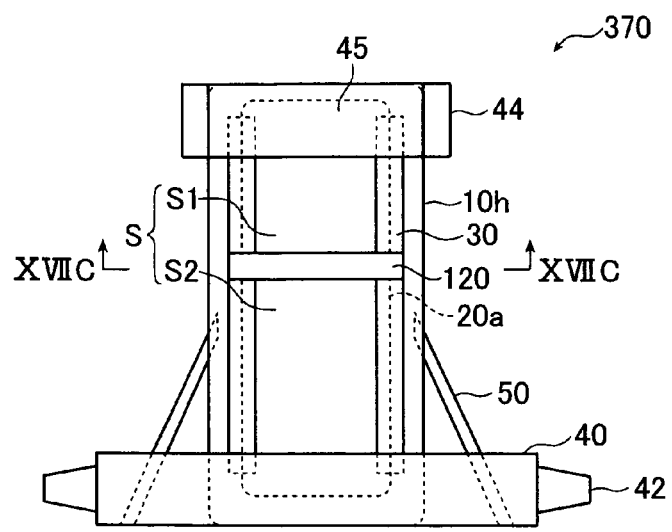
[FIG. 17] Schematic views each showing another example of an absorbent article according to the first aspect of the present invention.
Figure 17:
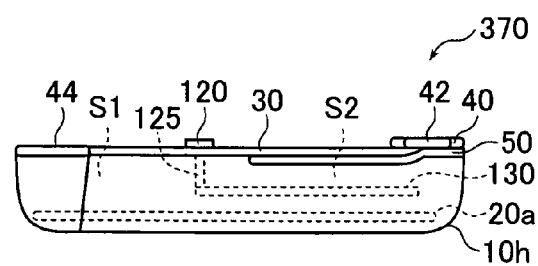
Figure 17:
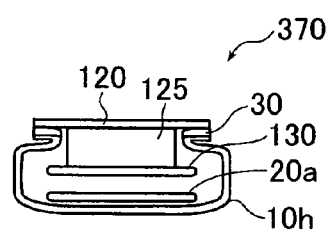

FIG. 17 are schematic views each showing another example of an absorbent article according to the first aspect of the present invention. FIG. 17(A) is a plan view, FIG. 17(B) is a left-hand side view, and FIG. 17(C) is a cross-sectional view taken along the line XVIIC-XVIIC of FIG. 17(A).

FIG. 17 show an absorbent article 370, which is basically the same as the absorbent article 100 and which is further provided with a bridge member 120 extending between the portions of the pair of side edge stretchable bands 30 corresponding to the crotch part.

While, in the absorbent article 370 shown in FIG. 17, the bridge member 120 is in contact with the upper surfaces of the side edge stretchable bands 30, in the present invention, the bridge member may also be in contact with the lower surfaces of the side edge stretchable bands; further, the bridge member may also be in contact with both the upper and lower surfaces of the side edge stretchable bands.

The bridge member 120 serves to connect the pair of side edge stretchable bands 30 to thereby maintain a fixed distance between them. As a result, there is little room for expansion in the lateral direction as in the case of conventional inner gathers or outer gathers, and the bottom surface part of a leak preventer 10h and the body surface of the wearer are held in contact with each other only in a relatively small area, so wetting of the lower half of the body, in particular, the front portion thereof, due to urine discharge is lessened; further, staining of the hips due to discharge of feces does not easily occur.

To attain this effect, it is desirable to properly determine the distance between the pair of side edge stretchable bands 30. For example, in the case of male use, it is desirable for the distance to be one allowing accommodating the penis and testicles in the internal space S. In the case of female use, it is desirable for the distance to be one allowing accommodating the labia major a in the internal space S. In any case, it is desirable not to leave much room in the lateral direction of the internal space S.

There are no particular limitations regarding the material of the bridge member 120 as long as it can maintain the form of the absorbent article in the lateral direction to a certain degree.

Examples of a preferred material include foams of PE, PP, polyurethane or the like, one obtained by covering the same with nonwoven fabric (e.g., hydrophobic nonwoven fabric), and one obtained by covering the same with a combination of a fiber bundle (e.g., sliver) and nonwoven fabric (e.g., hydrophobic nonwoven fabric). It is desirable for the bridge member 120 to be thick enough to exert a cushioning property.

Figure 18:
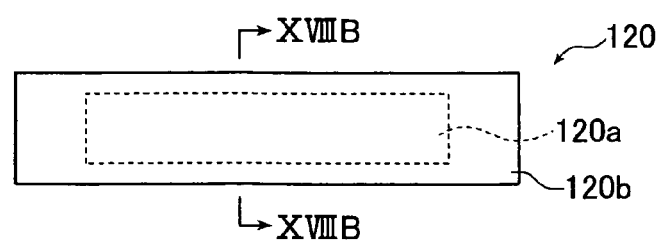
[FIG. 18] Schematic views each showing an example of a bridge member.
Figure 18:
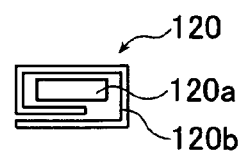

FIG. 18 are schematic views each showing an example of the bridge member 120. FIG. 18(A) is a plan view, and FIG. 18(B) is a sectional view taken along the line XVIIIB-XVIIIB of FIG. 18(A).

The bridge member 120 shown in FIG. 18 is formed by a core member 120a and a cover member 120b covering the same. The core member 120a is formed of urethane foam, and the cover member 120b is formed of nonwoven fabric.

For male use, there are no particular limitations regarding the length in the front-to-rear direction of the bridge member 120; for female use, it is desirable for the length to be 10 to 70 mm since it must be shorter than the distance between the urethral meatus and the anus of the wearer. For infant use, it is desirable for the length to be 5 to 40 mm.

While the bridge member 120 shown in FIGS. 17 and 18 are of a band-like (ribbon-like) configuration, there are no particular limitations in the present invention regarding the configuration of the bridge member as long as it helps to achieve the above-mentioned effect.

Above all, to improve the wearing comfort for the wearer, it is desirable to select a configuration and a material allowing the bridge member to be held in intimate contact with the perineum. Further, also in the case in which the bridge member provide a urine/feces separating function together with a separator described below, it is desirable to select a configuration and a material for the bridge member allowing it to be held in intimate contact with the perineum.

In a preferred mode for the case in which the absorbent article of the present invention is equipped with the bridge member, there is further provided a separator connected to the lower side of the bridge member, and the internal space is separated by the separator into a urine absorbing space on the front side and a feces receiving space on the rear side, with the absorber being arranged in the urine absorbing space (hereinafter, this mode will be referred to as "urine/feces separation structure").

In a preferred mode of the urine/feces separation structure, a water-resistant sheet is provided, for example, in the feces receiving space, and the front end portion of the water-resistant sheet is connected to the bridge member to thereby form the above-mentioned separator.

The absorbent article 370 shown in FIG. 17 is equipped with a water-resistant sheet 130, and the front end portion of the water-resistant sheet 130 is connected to the bridge member 120 via a connection member 125, whereby there is formed a separator connected to the lower side of the bridge member 120, and the internal space S is separated by the separator into a urine absorbing space S1 on the front side and a feces receiving space S2 on the rear side.

With this structure, urine is discharged into the urine absorbing space S1 and feces are discharged into the feces receiving space S2, with the separator therebetween, so it is possible to prevent mixing of urine and feces.

An absorber 20a is arranged in the urine absorbing space S1; it extends from the urine absorbing space S1 to the lower side of the water-resistant sheet 130 of the feces receiving space S2. Thus, in the feces receiving space S2, the absorber 20a is arranged between the leak preventer 10h and the water-resistant sheet 130.

The water-resistant sheet 130 is arranged in the feces receiving space S2.

There are no particular limitations regarding the material of the water-resistant sheet 130 as long as it is water-resistant enough to prevent displacement of urine to the feces receiving space S2 and displacement of feces to the urine absorbing space S1; it is desirable for the water-resistant sheet to exhibit a water resisting pressure of 50 mm/$H_2O$ or more, and more preferably, 100 mm/$H_2O$ or more.

Specific examples of the material include SMS, SB nonwoven fabric with surface rendered water-repellent, thermal bond nonwoven fabric, aperture film used as sanitary napkin surface material and relatively free from backward flow of liquid, and various materials used in the above-described leak preventer 10.

While the connection member 125 includes adhesive, there are no particular limitations in this regard in the present invention as long as it can physically prevent displacement of urine and feces. Examples of the material of the connection member include adhesive, rubber, film, foam, nonwoven fabric, and net-like sheet.

In the absorbent article 370 shown in FIG. 17, the pair of side parts of the leak preventer 10h are outwardly folded back at the ends, and the side edge stretchable bands 30 are formed thereon. Due to this structure, the absorber 20a and the water-resistant sheet 130 are not easily brought into contact with the body surface of the wearer, with the result that urine and feces discharged are not easily allowed to adhere to the body surface of the wearer.

Unlike the leak preventer 10 of the absorbent article 100, the leak preventer 10h shown in FIG. 17 is not folded.

Figure 19:
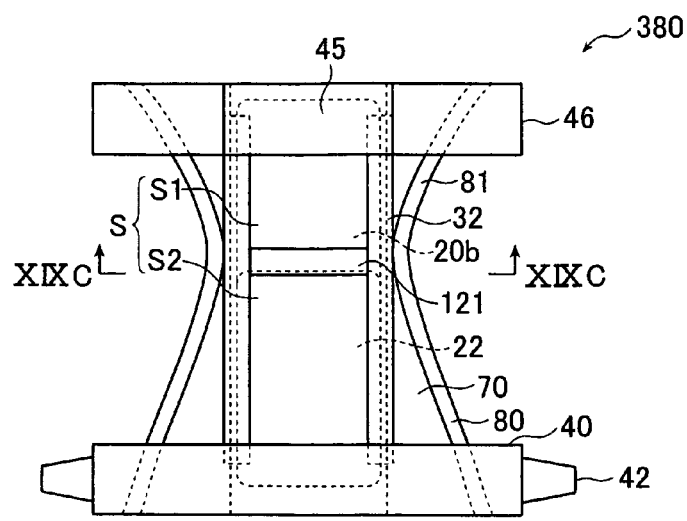
[FIG. 19] Schematic views each showing another example of an absorbent article according to the second aspect of the present invention.
Figure 19:
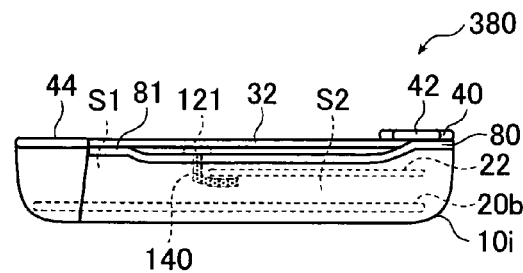
Figure 19:
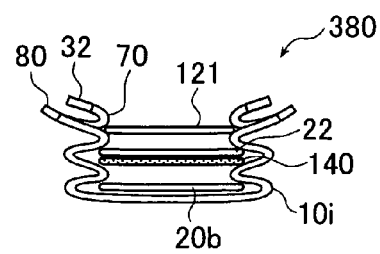

FIG. 19 are schematic views each showing another example of an absorbent article according to the second aspect of the present invention. FIG. 19(A) is a plan view, FIG. 19(B) is a left-hand side view, and FIG. 19(C) is a cross-sectional view taken along the line XIXC-XIXC of FIG. 19(A).

FIG. 19 show an absorbent article 380, which is basically the same as the absorbent article 200 and which is further provided with a bridge member 121 extending between the portions of the pair of side edge stretchable bands 32 corresponding to the crotch part.

In the absorbent article 380 shown in FIG. 19, the bridge member 121 is in contact with the lower surfaces of the side edge stretchable bands 32, except for which the bridge member 121 is the same as the bridge member 120.

In another preferred mode of the urine/feces separation structure, a second absorber is provided, for example, in the feces receiving space, and a urine guide member is provided in the vicinity of the front end portion of the second absorber, with the urine guide member being connected to the bridge member to thereby form the above-mentioned separator.

The absorbent article 380 shown in FIG. 19 is equipped with a urine guide member 140, which is connected to the bridge member 121 to thereby form a separator connected to the lower side of the bridge member 121, with the internal space S being separated by the separator into the urine absorbing space S1 on the front side and the feces receiving space S2 on the rear side.

When this structure is adopted, urine is discharged into the urine absorbing space S1, and feces are discharged into the feces receiving space S2, with the separator existing therebetween, so it is possible to prevent mixing of urine and feces.

An absorber 20b is arranged in the urine absorbing space S1; the absorber 20b extends from the urine absorbing space S1 to the lower side of a second absorber 22 in the feces receiving space S2; the pair of side parts are folded to divide the internal space S into upper and lower stages, and the absorber 20b exists in the lower stage.

The second absorber 22 is arranged in the feces receiving space S2. The pair of side parts are folded to divide the internal space S into upper and lower stages, and the second absorber 22 exists in the upper stage.

The second absorber 22 may be one similar to the absorber 20 mentioned above.

In the absorbent article 380 shown in FIG. 19, feces are received on the second absorber 22.

The urine guide member 140 is arranged in the vicinity of the front end portion of the second absorber 22. More specifically, the urine guide member 140 extends downwardly from the lower surface of the bridge member 121, and further extends to the rear to reach the lower side of the front end portion of the second absorber 22.

The urine guide member 140 serves to move the urine discharged into the urine absorbing space S1 to the feces receiving space S2 at the rear. Thus, the urine absorbing efficiency of the rear portion of the absorber 20b and the second absorber 22 is enhanced, whereby the urine absorbing efficiency of the absorbent article as a whole is enhanced.

Further, when urine moves rearward on the body surface of the wearer to reach the bridge member 121 and is prevented from making further rearward movement by the bridge member 121, which is in intimate contact with the perineum, the urine guide member 140 allows the urine to move along the surface of the urine absorbing space S1 side thereof to be smoothly absorbed by the absorber 20b, whereby the urine is prevented from leaking to the right or left from the position of the bridge member 121.

There are no particular limitations regarding the urine guide member 140 as long as it is of a structure allowing urine transfer. Specific examples of a preferred urine guide member include a molded film with concavity and convexity structure and a sheet of a double layer structure of a hydrophilic layer and a water-resistant layer. Examples of the sheet of a double layer structure of a hydrophilic layer and a water-resistant layer include a sheet obtained through lamination of a PE film constituting the water-resistant layer and a hydrophilic nonwoven fabric constituting the hydrophilic layer. To efficiently exert the urine/feces separating function and the urine transferring function, it is desirable for the sheet of a double layer structure of a hydrophilic layer and a water-resistant layer to be arranged such that the hydrophilic layer is on the urine absorbing space S1 side and that the water-resistant layer is on the feces receiving space S2 side.

Figure 20:
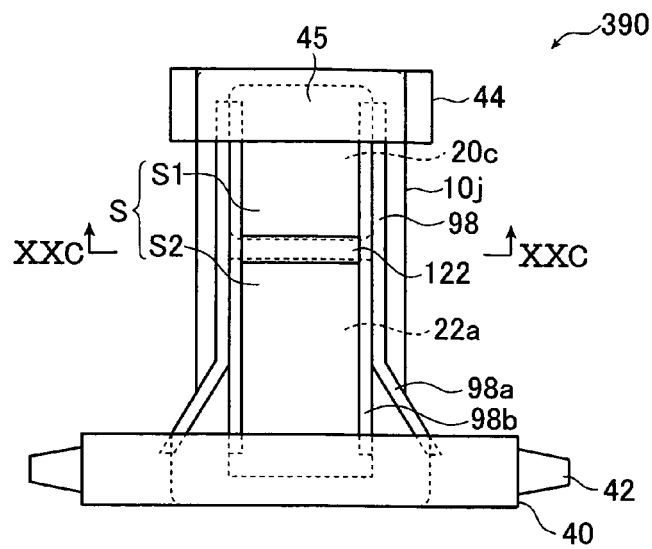
[FIG. 20] Schematic views each showing another example of an absorbent article according to the first aspect of the present invention in which the side edge stretchable bands and the hip wrapping stretchable bands are integrated.
Figure 20:
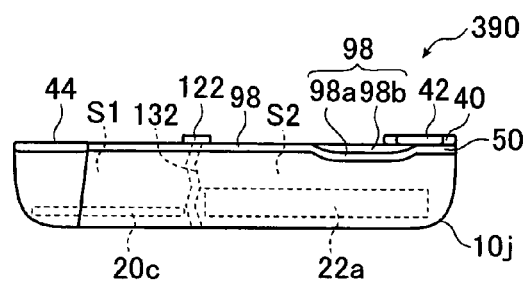
Figure 20:
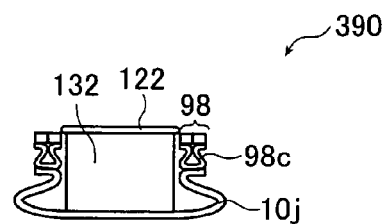

FIG. 20 are schematic views each showing another example of an absorbent article according to the first aspect of the present invention in which the side edge stretchable bands and the hip wrapping stretchable bands are integrated with each other. FIG. 20(A) is a plan view, FIG. 20(B) is a left-hand side view, and FIG. 20(C) is a cross-sectional view taken along the line XXC-XXC of FIG. 20(A).

In an absorbent article 390 shown in FIG. 20, which is basically the same as the absorbent article 320, there is further provided a bridge member 122 to extend between the portions of a pair of side edge stretchable bands 98 corresponding to the crotch part. The bridge member 122 is similar to the bridge member 120.

In another example of a preferred mode of the urine/feces separation structure, for example, the separator is a water-resistant sheet connected to the bottom surface part of the leak preventer.

In the absorbent article 390 shown in FIG. 20, a water-resistant sheet 132 is connected to the lower side of the bridge member 122 and is connected to the bottom surface part of a leak preventer 10j to form a separator, with the internal space S being separated by the separator into a urine absorbing space S1 on the front side and a feces receiving space S2 on the rear side.

With this structure, urine is discharged into the urine absorbing space S1, and feces are discharged into the feces receiving space S2, with the separator therebetween, so the urine and the feces are prevented from being mixed with each other.

An absorber 20c is arranged in the urine absorbing space S1.

Inside the feces receiving space S2, there is arranged a second absorber 22a. The second absorber 22a may be one similar to the absorber 20 mentioned above.

While there are no particular limitations regarding the combination of the absorber 20c and the second absorber 22a, it is desirable that the absorber 20c be a super absorbent sheet obtained by coating a body-fluid-permeable sheet of non-woven fabric or the like with SAP-dispersed slurry (e.g., MegaThin (Japanese registered trademark) manufactured by Japan Absorbent Technology Institute), and that the second absorber 22a be a super absorbent sheet obtained by the Air Laid process (e.g., B-SAP manufactured by Oji Kinocloth, Co., Ltd.). When the second absorber 22a is a super absorbent sheet obtained by the Air Laid process, due to the use of pulverized wood pulp, it is relatively bulky, so even when loose feces are discharged into the feces receiving space S2, they can be taken in by the second absorber 22a, making it possible to suppress staining of the body surface of the wearer.

The material of the water-resistant sheet 132 may be the same as that of the water-resistant sheet 130.

There are no particular limitations regarding the configuration of the water-resistant sheet functioning as a separator as long as it is connected to the lower side of the bridge member and connected to the bottom surface part of the leak preventer to exert a urine/feces separating function; however, as in the case, for example, of the water-resistant sheet 132 shown in FIG. 20, it is desirable for its length in the vertical direction to be somewhat larger than the distance between the lower surface of the bridge member 122 and the upper surface of the bottom surface part of the leak preventer 10j. This allows deformation of the absorbent article 390 according to the posture of the wearer. Further, it is possible to increase the capacity for temporarily storing urine in the urine absorbing space S1 when urine is discharged in a large quantity. Further, the feces receiving capacity of the feces receiving space S2 increases.

In the absorbent article of the present invention, it is possible to provide a skin contact sheet on the absorbent. When a skin contact sheet is provided, it is possible to attain a superior feel of a surface thereof during wear. There are no particular limitations regarding the skin contact sheet as long as it is body-fluid-permeable; it is possible to use a well-known sheet that has conventionally been used as a top sheet. Specific examples of the material of the skin contact sheet include synthetic fiber nonwoven fabrics such as PP nonwoven fabric, PET nonwoven fabric, and PE nonwoven fabric. Further, it is also possible to use a nonwoven fabric by carding method including a mixture of hydrophilic fiber such as rayon or cotton and synthetic fiber.

As described above, the absorbent article of the present invention has been described in detail based on the embodiment modes shown in the drawings. However, the present invention is not limited thereto, and structures of the respective members may be replaced by arbitrary structures which may exhibit similar functions.

The structures of the respective members of embodiment modes may be combined arbitrarily as other embodiment modes.

The absorbent article of the present invention may suitably be used as an absorbent article for an adult male, an adult female, or a child.

The invention claimed is:

1. An absorbent article, including:
    a leak preventer in sheet form having a bottom surface part and a pair of side parts raised upward from both the right and left sides of the bottom surface part and forming an internal space by the bottom surface part and the pair of side parts;
    an absorber arranged in the internal space at least in one layer, containing a super absorbent polymer, and capable of absorbing body fluid;
    a pair of side edge stretchable bands provided to extend along edge parts of the pair of side parts;
    a waist band joined to a rear end of the leak preventer and extending in a lateral direction; and
    a pair of hip wrapping stretchable bands connected to the pair of side parts of the leak preventer and/or the pair of side edge stretchable bands and to the waist band, in which:
    connection parts of the pair of hip wrapping stretchable bands to the pair of side parts of the leak preventer and/or the pair of side edge stretchable bands are positioned at a rear beyond a crotch part; and
    an interval between the pair of hip wrapping stretchable bands where they are connected to the waist band is larger than an interval between the pair of hip wrapping stretchable bands where they are connected to the pair of side parts of the leak preventer and/or the pair of side edge stretchable bands.

2. The absorbent article according to claim 1, in which the hip wrapping stretchable bands are integral with the side edge stretchable bands.

3. An absorbent article, including:
    a leak preventer in sheet form having a bottom surface part and a pair of side parts raised upward from both right and left sides of the bottom surface part and forming an internal space by the bottom surface part and the pair of side parts;
    an absorber arranged in the internal space at least in one layer, containing a super absorbent polymer, and capable of absorbing body fluid;
    a pair of inner walls provided on inner sides of the pair of side parts;
    a pair of side edge stretchable bands provided to extend along edge parts of the pair of inner walls;
    a waist band joined to a rear end of the leak preventer and extending in a lateral direction; and
    a pair of hip wrapping stretchable bands provided to extend along edge parts of the pair of side parts and connected to the waist band,
    in which an interval between the pair of hip wrapping stretchable bands where they are connected to the waist band is larger than an interval between the pair of hip wrapping stretchable bands at a crotch part.

4. The absorbent article according to claim 1, in which the side edge stretchable bands are connected to the waist band.

5. The absorbent article according to claim 1, in which the side edge stretchable bands include composite bodies formed by covering, with a nonwoven fabric, one or both sides of a plurality of thread-like elastic members arranged in parallel.

6. The absorbent article according to claim 1, in which:
the waist band has a width of 30 to 200 mm;
the side edge stretchable bands have a width of 10 to 100 mm; and
the hip wrapping stretchable bands have a width of 5 to 50 mm.

7. The absorbent article according to claim 1, in which at least a part of the waist band is a stretchable member.

8. The absorbent article according to claim 7, in which the waist band has a region of small tensile stress and a region of large tensile stress in that order from a side nearer to the leak preventer to a side farther therefrom.

9. The absorbent article according to claim 7, in which the waist band has a region of small tensile stress, a region of medium tensile stress, and a region of large tensile stress in that order from a side nearer to the leak preventer to a side farther therefrom.

10. The absorbent article according to claim 7, in which the waist band has a region of small tensile stress, a region of large tensile stress, and a region of medium tensile stress in that order from a side nearer to the leak preventer to a side farther therefrom.

11. The absorbent article according to claim 7, in which the waist band has a non-stretchable member at a center in a lateral direction and stretchable members on left and right sides of the non-stretchable member, with the non-stretchable member being connected to the leak preventer.

12. The absorbent article according to claim 7, in which the waist band is connected to the leak preventer in a lateral direction by a plurality of connection parts.

13. The absorbent article according to claim 12, in which a length of the leak preventer is larger than a length of the waist band between each of the plurality of connection parts.

14. The absorbent article according to claim 1, further including:
a front waist band connected to a front end of the leak preventer and extending in a lateral direction; and
a pair of front stretchable bands connected to the pair of side parts of the leak preventer and/or the pair of side edge stretchable bands and to the front waist band,
in which an interval between the pair of front stretchable bands where they are connected to the front waist band is larger than an interval between the pair of front stretchable bands where they are connected to the pair of side parts of the leak preventer and/or the pair of side edge stretchable bands thereof.

15. The absorbent article according to claim 1, in which the waist band is annular, and is connected to a rear end and a front end of the leak preventer.

16. The absorbent article according to claim 15, further including a pair of front stretchable bands connected to the pair of side parts of the leak preventer and/or the pair of side edge stretchable bands and to a front end side of the leak preventer of the waist band,
in which an interval between the pair of front stretchable bands where they are connected to the waist band is larger than an interval between the pair of front stretchable bands where they are connected to the pair of side parts of the leak preventer and/or the pair of side edge stretchable bands thereof.

17. The absorbent article according to claim 14, in which the front waist band has a width of 5 to 50 mm.

18. The absorbent article according to claim 1, further including a bridge member provided to extend between portions corresponding to the crotch parts of the pair of side edge stretchable bands.

19. An absorbent article according to claim 18, in which the bridge member is in contact with upper surfaces of the side edge stretchable bands.

20. The absorbent article according to claim 18, in which the bridge member is in contact with lower surfaces of the side edge stretchable bands.

21. The absorbent article according to claim 18, further including a separator connected to a lower side of the bridge member, in which:
the internal space is divided by the separator into a urine absorbing space on a front side and a feces receiving space on a rear side; and
the absorber is arranged in the urine absorbing space.

22. The absorbent article according to claim 21, in which:
a water-resistant sheet is provided in the feces receiving space; and
a front end portion of the water-resistant sheet is connected to the bridge member to thereby form the separator.

23. The absorbent article according to claim 22, in which, in the feces receiving space, the absorber is arranged between the leak preventer and the water-resistant sheet.

24. The absorbent article according to claim 21, in which:
a second absorber is provided in the feces receiving space;
a urine guide member is provided in a vicinity of a front end portion of the second absorber; and
the urine guide member is connected to the bridge member to thereby form the separator.

25. The absorbent article according to claim 21, in which the separator is a water-resistant sheet connected to the bottom surface part of the leak preventer.

* * * * *